United States Patent [19]
Yadav et al.

[11] Patent Number: 5,952,040
[45] Date of Patent: Sep. 14, 1999

[54] PASSIVE ELECTRONIC COMPONENTS FROM NANO-PRECISION ENGINEERED MATERIALS

[75] Inventors: Tapesh Yadav; Mark L. Yang, both of Tucson, Ariz.

[73] Assignee: Nanomaterials Research Corporation, Longmont, Colo.

[21] Appl. No.: 08/730,661

[22] Filed: Oct. 11, 1996

[51] Int. Cl.[6] .............................. B05D 5/12; B05D 3/02; B05D 1/36
[52] U.S. Cl. ................ 427/126.3; 427/125; 427/79; 427/376.2; 427/419.2; 427/189
[58] Field of Search ................ 427/125, 126.3, 427/376.2, 419.2, 79, 189; 156/73.1, 306.3

[56] References Cited

U.S. PATENT DOCUMENTS

| | | | |
|---|---|---|---|
| 4,426,356 | 1/1984 | Nair | 419/21 |
| 4,453,199 | 6/1984 | Ritchie et al. | 361/306 |
| 5,258,338 | 11/1993 | Maher | 501/137 |
| 5,414,588 | 5/1995 | Barbee, Jr. et al. | 361/304 |
| 5,486,277 | 1/1996 | Barbee, Jr. et al. | 204/192.15 |
| 5,560,960 | 10/1996 | Singh et al. | 427/222 |
| 5,590,387 | 12/1996 | Schmidt et al. | 419/36 |

OTHER PUBLICATIONS

Eastman et al., "Processing and Properties of Nanophase Oxides," Mater Res. Soc. Symp. Proc., 155, 255, 1989.

*Primary Examiner*—Shrive Beck
*Assistant Examiner*—Michael Barr
*Attorney, Agent, or Firm*—Sam Pasternack; Karoline K. M. Shair; Choate, Hall & Stewart

[57] ABSTRACT

Nanosize powders with particle size smaller than the critical length for specific material properties are used to form the ceramic layers of passive electronic components. Ceramic substrates are coated with electrodes, which are then coated with a ceramic layer from a suspension, preferably a low viscosity suspension, of nanoscale powders. The ceramic layer is dried at low temperatures (preferably below 200° C.) and it is sintered to high density (preferably above 90%) at moderate temperatures (preferably low and less than 1,000° C.). Once sintered, an electrode layer is coated on top of the ceramic layer to yield an electrode/ceramic/electrode structure.

21 Claims, 15 Drawing Sheets

PASSIVE ELECTRONIC COMPONENTS FROM NANO-PRECISION ENGINEERED MATERIALS

BACKGROUND OF THE INVENTION

1. Field of the Invention

This invention pertains in general to processes and materials for manufacturing passive electronic components. In particular, the invention relates to a novel approach for the manufacture of capacitors, varistors, resistors, inductors, and EMI filters utilizing band gap confined, nano-precision engineered materials.

2. Description of the Prior Art

In the field of electronics, passive devices such as capacitors, resistors, inductors, varistors, and EMI filters are essential components of various products and services provided by the electronics, information processing, communications, energy management, and electrical industry. For example, all modern computers, automobiles, aircrafts, communication networks and power plants utilize these components in large numbers. It is estimated that more than a hundred billion passive components are manufactured and sold every year on a world wide basis, and that the passive electronic component market in the United States exceeds $30 billion for the manufacture of products with sales in excess of $350 billions. Thus, the passive electronic component industry is fundamental to the welfare of the U.S. and world economies and any improvement in the method of manufacture or in the properties of passive components is very desirable and becoming increasingly necessary.

Existing technologies for manufacturing passive components were developed empirically at the beginning of the electronic industry over five decades ago, with significant but only incremental improvements having been achieved since then. The devices so produced have been satisfactory to meet the current needs of customers, but the recent unprecedented growth and changes in the industries utilizing passive electronic components are increasingly requiring levels of performance that conventional technologies cannot provide. For example, dramatically increasing processing speeds and operating frequencies and the unremitting need for foot print reduction of active electronic components compel progressive miniaturization for surface mount engineering and for high-frequency operation. This trend is demonstrated by the major increase in market share of miniature 0402 ceramic capacitors (0.04 inches long×0.02 inches wide) over the last ten years, while larger sizes, such as 0805 ceramic capacitors, have lost significant market share. However, such desirable performance characteristics cannot be met economically by current production processes and materials. Current surface mount passive components in various formulations do not offer the capacitance, resistance, inductance, EMI reduction, temperature coefficient of capacitance, temperature coefficient of resistance, temperature coefficient of inductance, break down voltage, loss factor, dissipation factor, spectrum conservation, cross talk, compatibility with conductor termination, and frequency response desired by industry. Consequently, either the performance of the intended final product is reduced in order to design around these inherent problems, or more and more volume and weight are added to the final product to account for passive electronic component requirements. With ever-growing reductions in center to center spacing of active components and with the evolution to higher frequencies in computers, higher baud rate over Internet and World Wide Web, wireless data transfer, and cellular communication, this problem represents a technology barrier.

The present invention is directed at solving this problem by employing new fabrication methods and materials based on nanosize powders such as those described in the referenced copending applications. As would be apparent to one skilled in the art, the present disclosure is presented with reference to capacitors, resistors, inductors, and varistors and improved methods for manufacturing them, but it is applicable to all types of passive electronic devices that comprise a thin layer of ceramic material as an active component. Therefore, to the extent that this invention is also applicable to capacitor arrays, resistor arrays, inductor arrays, varistor arrays, EMI filters, thermistors, piezo-devices, ceramic magnets, thermoelectric devices, ion-conducting electrolytes, batteries, and sensors, it is not intended to be limited to the manufacture of capacitors, resistors, inductors and varistors.

In response to the growing need for better performing capacitors, research and development efforts have focused on the discovery of novel materials with very high permittivity [see D. Finello, "New Developments in Ultracapacitor Technology," The 4th International Seminar on Double Layer Capacitors and Similar Energy Storage Devices, Boca Raton, Fla., December (1994)], the rationale being that high permittivity would lead to improved capacitor performance. Despite these efforts and several laboratory successes, though, these new materials have not found much market acceptance and the predominant ceramic dielectrics used in industry continue to be material formulations based on $BaTiO_3$, $SrTiO_3$ and $TiO_2$. Although most new materials have a substantially increased K value, they often do not also have acceptable temperature stability (such as one matching the X7R standard); reliability data on capacitors manufactured with new materials are either not available or not sufficient to convince users of a failure rate smaller than 10 ppm, as required for acceptance in the industry; some of these materials are based on elements with too limited long-term supply for large scale use (e.g. Ruthenium); some materials are not readily suitable for large-scale automated production; and all materials are too expensive for an acceptable performance-to-cost ratio.

Therefore, the market has been reluctant to change to these new materials. Instead, techniques that have found market acceptance are those that have aimed at improving the performance of existing capacitors without changing the dielectric material. In broad terms, these techniques have involved producing ultra-thin ceramic capacitors by eliminating inhomogenities in the micron-sized dielectric layers; reducing particulate impurities in the dielectric powders used to form the dielectric layers and in the manufacturing process; and modifying raw material characteristics and manufacturing techniques to achieve electrical and mechanical strengths that are close to the theoretical values of currently used capacitor materials. The rationale for these approaches is simply based on the fact that energy density of a capacitor inversely depends on the square of the dielectric layer's thickness; that is, a reduction to one half in dielectric thickness enhances the energy density by a factor of four. Similarly, since the power density of a capacitor is a strong function of the capacitor's equivalent series resistance and inductance, both of which are a strong function of dielectric layer thickness and electrode properties, a reduction in the layer thickness can also significantly improve the power density of a capacitor. A reduction in layer thickness also reduces the device's size and weight, which is very important for applications where space and mass are premium quantities that significantly affect the overall system performance, such as in computers, portable communication, information network, and aerospace electronics. U. S. Pat. No. 5,486,277 discloses a process for manufacturing high performance capacitors by controlled sputtering of dielectric and electrode material to form a nanostructured multilayered device.

Efforts aimed at reducing particulate impurities are also significant because it is now well known that material impurities are the main cause of capacitor failure. Finally, the mechanical and electrical strength of existing capacitors is being enhanced by producing more uniform micropowder of dielectrics and by reducing adverse effect of binders. In summary, technologies that yield ultra-thin, reliable dielectric layers with less tendency to break down electrically, thermally, mechanically, or chemically during manufacturing and use, are more acceptable to and desired by the market.

Another aspect of passive-component ceramic processing addressed by this invention is the problem related to the process temperature requirements of conventional materials and manufacturing methods. As would be apparent to those skilled in the art, conventional materials and manufacturing methods require high sintering temperatures and long sintering times to form reliable, high-density ceramic layers for passive electronic components. The sintering temperature requirements often exceed 1050° C. and sintering times last hours. This not only leads to increased energy costs, increased inventory costs, and increased pollution, but also limits the choice of electrode materials to expensive alloys. More specifically, the electrode composition of passive electronic components is limited to metals and alloys that can withstand temperatures in excess of 1050° C., often exceeding 1,100° C., such that these electrode layers can survive the sintering temperature of conventionally produced ceramic materials for electronic applications. Electrodes typically consist of a Pd/Ag alloy with some use of Pt, Cu, and Ni for special applications. This choice is an engineering trade-off between the high melting point, but high cost, of Pd and the low melting point, but low cost, of Ag. The addition of Pd (or Pt) raises the melting point of the alloy, thereby satisfying the necessity for a high melting point to meet the dielectric materials' sintering requirements. However, the low cost and a desire to utilize the excellent electrical properties of Ag (which, unfortunately, has a low melting point −960° C.) have provided an incentive for using the highest possible concentration of Ag. In summary, it has been a market trend and a market need to prepare and use ceramic material formulations that offer lower sintering temperatures.

With reference to varistors, current design and production technology also present some serious limitations. Like capacitors, the varistor production process begins by mixing micron-sized powders corresponding to a given ceramic material formulation. The dominant ceramic composition for varistors is based on ZnO and $SrTiO_3$, supplemented with additives such as $Bi_2O_3$, CoO, MnO, $Cr_2O_3$, and $Sb_2O_3$. The powders are milled in deionized water. The mix is then typically blended with PVA and spray dried. The resulting granulated powder is pressed to disc (or any other desired shape) with a diameter ranging between 0.4 and 10 cm and a thickness ranging between 0.1 and 4 cm. The pressed pellet is sintered at about 1,200° C. in air and then metallized to make electrodes on the disc faces. The electrode surface is then soldered with leads for connections. Alternatively, multilayer varistor devices are prepared, like capacitors, by stacking layers of ceramics separated by electrode layers. Finally, this assembly is environmentally and mechanically protected by encapsulation using a conforming coating or other packaging techniques.

Research and development efforts in the field of varistors have focussed on the discovery of novel additives and materials, on heat treatment methods to control grain growth, on disc thickness reduction, on layer thickness reduction, on sintering temperature reduction, and on formation techniques for multilayer varistors, for low voltage and high frequency applications. Despite these efforts, current varistor technology continues to face several limitations. Existing varistors are bulky, with diameters between 0.4 cm and 10 cm, and thicknesses of 0.1 cm to 4 cm. This size limitation is significant in applications, such as for computers, portable communication, information network, and aerospace electronics, where weight and space are important considerations. Furthermore, the trend towards miniaturization of solid-state devices imposes further size reduction requirements on existing varistor technology. The capacitance range of current varistors is between 50 pF and 5000 pF, which precludes operation in high frequency applications. In addition, ZnO varistors typically feature a 3 V/grain voltage drop; therefore, the threshold voltage for ZnO varistors is often over 10 volts. This makes it difficult to integrate miniature varistors with electronic components and devices working at voltages below 10 V. The use of $SrTiO_3$ may provide a material breakthrough because it features a voltage drop of 1.3 V/grain. However, the size and frequency limitations apply also to $SrTiO_3$ varistors.

The ceramic powders used for varistor manufacturing have grain sizes from 1 µm to as large as 10 to 25 µm. As a result, the sintering step during varistor manufacturing necessarily requires temperatures in the 1100 to 1300° C. range, which leads to significant grain growth. Given the inherent limitations associated with the size of precursor powders, the only strategy that is practically available with prior-art technology to achieve a high reference breakdown limit voltage is to increase the varistor thickness (i.e. make the varistor bulky).

Attempts to miniaturize varistors for low voltage applications are also limited by the powder size. Like capacitors, in varistors the ceramic layer thickness is a function of the starting ceramic powder size. Thus, while electronic devices are increasingly reducing in foot print size and line to line spacing to sub-micron levels, the varistor component cannot be reduced beyond a size of a few microns. Finally, the present invention also addresses the unsatisfactory performance of conventional varistors in high frequency applications. This limitation can be traced back to large grain sizes and to the increase of losses with increases in grain size and frequency.

With reference to resistors, existing precursors (e.g. resistor inks) that are used to prepare film resistors are based on micron-sized powders. More specifically, the blend often consists of glass frit, electrically conducting powder, additives and an organic screening agent. The existing resistor inks are increasingly proving to be a design limitation where very low sheet resistivities and high frequencies are required. Furthermore, with ongoing and anticipated device miniaturization, higher density packing of circuit features and consequent reduction in footprint, it is expected that existing resistor fabrication technology will be limited by micron sized powders being used as resistor precursors.

Users of passive electronic components desire resistors with high sheet resistance, high frequency response, high power dissipation, and high voltage operability, which is difficult to achieve with conventional materials in miniaturized resistors. The teachings of this invention are also applicable to satisfy this need and to improve other performance limitations in resistor technology, such as low temperature coefficient of resistivity (TCR), high short-time overLoad voltage (STOLV), low current noise, minimum permanent changes in resistance with elevated temperatures, humidities and stress, compatibility with conductor terminations, and low processing sensitivity.

With respect to inductors, the ceramic materials of choice are often ferrites and rare earth borides. Once again, like capacitors, varistors and resistors, conventional inductor manufacturing is based upon the use of micron-sized powders of magnetic ceramics. The micron-sized magnetic ceramic powders are usually prepared by milling, attrition, precipitation, or a combination of these techniques. The powders are formulated with additives and processing aids, processed into desired shapes such as layers, discs, chips, toroids, and tubes. The material is then provided with an electrode layer to form the single layer inductive component. For multilayers, alternating layers of magnetic ceramic and electrodes are provided. The device is then singulated, if needed, and sintered at temperatures in excess of 1050° C. As a final step, the device is often environmentally shielded with a layer of protective material, usually a polymer.

This invention addresses the limitation in existing inductors to operation at low frequencies and low energy densities, and the limitations to miniaturization and reduction of inductors' foot print. Like capacitors, varistors and resistors, conventional inductors prepared from micron sized powders are limited in final component foot print to sizes that are multiples of the starting powder size (that is, multiples of microns). In the case of multilayered components, final component foot prints are limited to sizes that are even larger (often multiples of millimeters). In addition, this invention addresses the need for materials with higher resistivity and higher initial permeability.

Regarding EMI filters, these passive components are extensively used to filter noise, reduce cross talk, preserve electromagnetic spectrum in electronic, electrical, information, computing, and magnetic devices. As would be apparent to the skilled in the art, an EMI filter is a combination of resistive, inductive, and capacitive elements. Therefore, all problems and limitations in these components are also applicable to EMI filters. Consequently, existing EMI filter components exhibit poor performance at high frequencies, are bulky, expensive to manufacture, and are difficult to miniaturize.

Thus, recent competitive trends in passive electronic component manufacturing have been towards making the thickness of each layer in the component thinner, reducing the sintering temperatures so as to increase the use of Ag as electrode material, enhancing the material properties, reducing component costs, increasing component reliability, and improving the productivity of each processing step. A technological breakthrough that enabled greater miniaturization and provided improved high-frequency performance characteristics would be very desirable. The present invention provides a novel approach that greatly improves these aspects of passive electronic component performance and manufacture.

SUMMARY OF THE INVENTION

One of the objectives of this invention is a process and materials that permit the manufacture of passive electronic components having thinner ceramic layers than attainable with conventional methods.

Another objective of this invention is a process and materials that permit the manufacture of passive electronic components having thinner electrode layers than attainable with conventional methods.

Another object of the invention is a process and materials that require lower than conventional sintering temperatures of the ceramic layers of passive electronic components (preferably less than 950° C.), thereby making it possible to utilize higher amounts of silver and other low-melting-point, low-cost metals as the electrode material of choice for such electronic components.

Another goal is a process and materials that yield ceramics with improved properties (permittivity, permeability, resistivity, voltage breakdown per interface, processability) and performance characteristics for passive electronic component applications.

Still another goal is a process and materials that facilitate the miniaturization of passive electronic components.

A further goal of this invention is a process and materials that can lead to passive electronic components that can operate over wide frequency ranges, preferably beyond 100 MHz.

Another objective is a process that is suitable for large production rates because it utilizes materials that are readily available in large quantities, in the order of tons per day.

Another goal of this invention is a process and materials that permit manufacturing of post-sintered ceramic and electrode layers with microstructure less than 1 micron.

Yet another objective is a process that is environmentally advantageous by reducing the use of environmentally undesirable chemicals and additives normally utilized in conventional passive-electronic-component processes.

Another goal is a process and materials that reduce the cost, inventory, and time needed to manufacture passive electronic components.

A further goal is a process that is flexible, so as to allow the production of multiple products with relatively simple operating changes.

Finally, another goal is a process that can be affordably integrated with conventional methods and infrastructure for manufacturing passive electronic components.

Therefore, according to the foregoing objectives, one aspect of this invention involves the use of nanostructured precursors (narrowly distributed nanosize powders with mean grain size preferably less than 100 nm and standard deviation preferably less than 25 nm) to form the ceramic layers, electrode layers, or both, in passive electronic components. The process of the invention starts by forming an electrode layer on a substrate from conventional electrode materials, nanostructured electrode precursors, or a composite of nanostructured electrode precursors and conventional electrode materials provided through either single phase fluid or multiple phase suspension feed. Materials useful as substrate for the present invention include those that maintain their integrity at the temperatures and pressures imposed upon them during any deposition and sintering steps of subsequent processing. The substrate may be flexible or rigid, organic or inorganic, planar or non-planar. The electrode layer is dried (preferably below 200° C.). Next, a ceramic layer is built onto the electrode by forming a thin film (preferably less than 1 micron) from nanostructured precursors provided through either single phase fluid or multiple phase suspension feed. The viscosity, density, concentration, and exposure time of the feed to the electrode surface is controlled to engineer the ceramic layer thickness.

In one version of the process, the ceramic layer is dried at low temperatures (preferably below 200° C.) and then sintered to high density (preferably above 90%) at moderate temperatures (preferably below 950° C.). Then another layer of electrode is formed, if required for the particular passive component, in a manner similar to the formation of the first electrode layer to yield an electrode/ceramic/electrode structure. The process is repeated to form multilayered components. In an alternative version of the process, the ceramic layer is dried (preferably below 200° C.), and then the next layer of electrode is deposited on the dried but not yet sintered (i.e., "green") ceramic film to yield an electrode/ceramic/electrode structure. If desired, more alternating layers of green ceramic and electrode are formed. Finally, the components are singulated and then sintered to high density (preferably above 90% of full density; i.e., 90% of theoretical density) at moderate temperatures (preferably below 950° C.). It is noted that pressure has no significant effect on the temperature required to densify the ceramic to a given percentage of full density; therefore, no reference is made herein to operating pressure, but it is understood that the sintering process could be equivalently carried out at temperatures above or below atmospheric.

To reduce this invention to practice, nanosize ceramic powders for passive electronic components were produced and characterized using transmission electron microscopy, X-ray diffractometry, BET adsorption, and energy dispersive spectroscopy. A set of capacitors, resistors, inductors, and varistors was prepared from nanostructured precursors and reproducibly characterized. The invention enabled passive component manufacturing at temperatures less than 950° C. and in less time, required significantly less amounts of Pd, produced layer thicknesses that were less than 1 micron, and post-sintered grain sizes less than 1 micron. The passive components so produced exhibited orders of magnitude improvements in properties and performance.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiments and particularly pointed out in the claims. However, such drawings and description disclose only some of the various ways in which the invention may be practiced.

BRIEF DESCRIPTION OF THE DRAWINGS

FIG. 4($b$) is a greatly magnified microscope image of the grain size of the dielectric film of FIG. 4($a$).

FIG. 7($b$) is a greatly magnified microscope image of the grain size of the dielectric film of FIG. 8($a$).

DETAILED DESCRIPTION OF THE INVENTION

Figure 1:
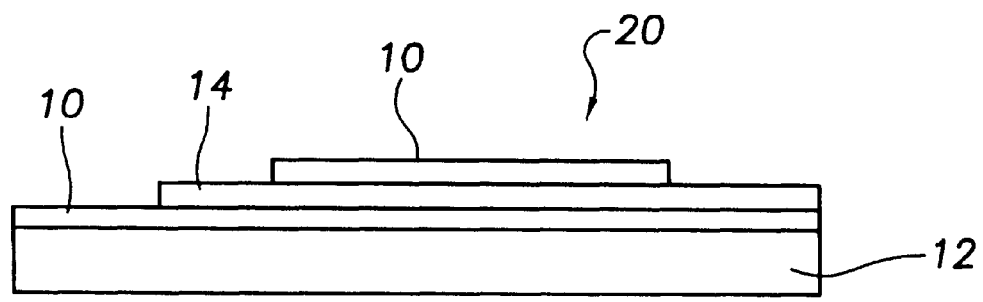
FIG. 1 is a schematic illustration of a passive-electronic-component electrode/ceramic structure manufactured with nanosize powder ceramics according to the present invention.

A primary aspect of this invention lies in the recognition that a standing barrier to markedly improved technology in the manufacture of passive electronic components exists in the limitations inherent with the grain size of the ceramic and electrode material used. The finest, low-cost ceramic powders currently available for commercial use consist of particles with sizes in the order of several microns. For example, the precursor $BaTiO_3$ and $TiO_2$ dielectric powders that are presently used in large quantitites to produce multilayered ceramic capacitors are 2–5 microns in size. Powders with mean size of about 1 micron are considered specialty powders, are difficult to produce, and are expensive. Since precursor powders are not ductile, the films of ceramic material have to be packed several grains thick and sintered to ensure that there are no pin-holes in the resulting ceramic and electrode layers. Thus, even though the theoretical limit with existing materials and manufacturing technology on the thickness of the ceramic layer is in the 2 to 5 μm range, current passive electronic components are routinely made with 5 to 20 μm thick ceramic layers. Attempts to reduce this thickness to the theoretical limit have resulted in problems of electrical, thermal, mechanical, or chemical breakdown with consequent reliability issues. Thus, it is clear that the minimum thickness of ceramic and electrode layers attainable with conventional processes is limited by the grain size of the precursor ceramic and electrode material.

Moreover, ceramics fracture easily under tensile stresses resulting from flexure and are difficult to fabricate as thin plates that would not fracture when a stack of them is subjected to the pressure necessary to form them into a solid block during conventional processing. Although this problem has been addressed by avoiding the stacking step and forming the block by alternate spraying of the dielectric and metal layers, such innovative processing methods are still unable to produce ceramic layers that are each less than a few microns thick.

Thus, the current inability to produce ultra-thin layers of passive electronic components is a result of the inability of prior-art processes to reduce powder size of precursor materials beyond the micron-size range, to process fine powders into thin layers conveniently, and to maintain mechanical strength of the component as layer thickness is reduced.

Another aspect of this invention is based on the insight that conventional passive electronic components are prepared from micron sized powders that exhibit bulk properties (permittivity, permeability, resistivity, voltage breakdown per interface, and processability). These properties in turn depend on fundamental electrical processes such as mean free path, skin depth, and domain size and these fundamental processes have their respective characteristic lengths for a given material composition and environmental condition. The critical idea of the invention then is to build passive components from powders whose grain size has been confined to dimensions less than the characteristic critical length for the fundamental property or process of interest. Thus, as those skilled in the art would readily understand, such characteristic length will be the mean free path of electrons in the material with respect to electrical resistivity and thermal conductivity; skin depth, with respsct to Eddy losses and AC permeability; domain size, with respect to ductility and magnetic properties, permittivity, and initial permeability; etc., as one skilled in the art could determine for any physical property of interest for a given material. The size confinement effects in nanometer scale can confine fundamental processes to band-gap and quantum confined states which in turn can dramatically change the properties and performance of the resulting passive electronic components. This insight can be implemented as ceramic devices prepared with one dimensional quantum dot and nanocluster composite with the dot size less than 100 nm (preferably less than 10 nm), as quantum wires with diameter less than 100 nm (preferably less than 10 nm), as quantized and nanoscale films with film thickness less than 100 nm, as nanostructured layers and pellets with microstructure less than 100 nm, and as a combination of these. In summary, the second aspect of the invention concerns the preparation of ceramic devices that are performing under interfacially confined state.

Premised on these realizations, the present invention is based on the utilization, as precursor material, of powders having a particle size smaller than the critical length characteristic of the property of interest for the material and on the preparation of nanostructured films for the fabrication of passive electronic components. The work disclosed in copending applications Ser. Nos. 08/706,819 and 08/707,341 now U.S. Pat. No. 5,788,738 which are commonly assigned, provides a viable vehicle for manufacturing nanoscale ceramic powders suitable for the present invention.

As defined in the art, submicron powders are materials having average grain size below 1 micrometer. Of critical interest for this invention are nanoscale powders and nanostructured layers of ceramics and electrodes. Nanoscale powders (nanopowders) are submicron powders with average grain size less than 100 nanometers (preferably with a standard deviation of less than 25 nm) and with a significant fraction of interfacial atoms. Accordingly, reference to nanoscale powders in this disclosure is intended to refer to powders with those characteristics, but it is understood that the critical length for a given property of a material may be smaller or larger, depending on the property of interest, although such length is always submicron.

Submicron layers are layers having thickness less than 1 micrometer. Of particular interest to this invention are nanostructured layers which are defined specifically as layers with thickness, or microstructure, or both, confined to a size less than property confinement size (positively less than 1 micron, preferably below 100 nm). Accordingly, reference to nanostructured layers in this disclosure is intended to refer to layers with those characteristics.

As discussed in the copending applications, it is known that within these size ranges a variety of confinement effects occur that dramatically change the properties of the material. A property will be altered when the entity or mechanism responsible for that property is confined within a space smaller than some critical length associated with that entity or mechanism. For example, a normally ductile metal will become significantly harder if its grain size is reduced to the point where moving dislocations through its crystal lattice are no longer able to occur at normal levels of applied stress. Since the stress required to produce a Frank-Read dislocation is inversely proportional to the spacing between its pinning points, as one skilled in the art would readily understand, a critical length in this case is that for which the stress necessary to produce a dislocation becomes larger than the conventional yield stress for the given material.

Thus, confinement effects can be exploited to produce extremely hard and strong materials with much higher yield stress than exhibited by the conventional form of their precursors. Nanostructured devices prepared from nanopowders feature grain sizes too small for Frank-Read dislocation to operate in the conventional yield stress domain and, consequently, enhancement in strengths and hardness of 100% to 500% are observed in films and pellets made from nanopowders (important to all passive components). Similarly, nanostructured layer devices with a grain size confined to a dimension less than the mean free path of electrons are expected to exhibit resistivities that are higher by orders of magnitude greater than conventional materials (important for resistors and EMI filters). If the nanostructured grains are confined to a dimension smaller than the domain size of magnetic materials, the resulting devices are expected to exhibit dramatically higher permeability (important to inductors and EMI filters), novel properties such as giant magneto-resistance (GMR), and superparamagnetic effects. Nanostructured grains are nanoscale and therefore enable the manufacture of ultrathin nanostructured layers of ceramic and electrode (important to capacitors, varistors, resitors, inductors and EMI filters) and greater miniaturization of all these devices.

Nanostructured materials also offer the opportunity for near-molecular blending of dopants and property modifiers. This is very important because commercial passive components are not prepared from a single component; instead, the ceramic layer is made of a formulation that consists of several components (from five to seventeen are reported in the literature), each added to provide the desired matrix of performance characteristics over the device's lifetime and usage environment. Near-molecular blending can enhance device reliability and reproducible performance, particularly when the device footprint keeps getting smaller. Nanoscale composites of electrodes can reduce the need for expensive alloys and yet ensure the desired electrical performance at miniaturized scale. Nanostructured electrodes also offer very high surface area and modified electrochemical properties, which are important for boundary layer and electrolytic passive components.

From a processing viewpoint, nanopowders offer very high surface area, which leads to enhanced interfacial diffusivities; enhanced diffusivities in turn enable rapid, low temperature consolidation, sintering, and forming of normally difficult-to-process materials. This effect is very important because it lowers the temperatures required for sintering and densifying the powder precursors laid to form ceramic layers. Densification by sintering is a necessary step to eliminate openings between grains of ceramic material that might cause failure of the ceramic layer and therefore of the passive electronic component. While sintering of dielectric materials prepared by prior-art processes requires temperatures in excess of 1,050° C., densification of the nanopowder layers formed by the process of the invention can be carried out at temperatures as low as 850° C.

The grain size of nanostructured materials is less than the wavelength of visible light; consequently, unique optical materials with grain sizes tailored for excitonic interactions with particular wavelengths can be prepared. Nanopowders are isomorphic because of dimensional confinement. Furthermore, enhanced solubilities are observed leading to non-equilibrium compositions. These characteristics offer the potential for catalysts with extremely high surface areas, high selectivity and activity. Finally, nanopowders feature quantum confinement to dimensions less than Debye length, which leads to electrochemical properties with order-of-magnitude higher sensitivities to chemical species.

Nanopowders, in summary, can enable the manufacture of nanostructured layers of ceramics, or alloys, or metals, or composites, or combinations thereof, and can lead to greater miniaturization of many devices. This approach can lead to devices with commercially desirable and unique properties (capacitor arrays, resistor arrays, inductor arrays, varistor arrays, EMI filters, thermistors, piezo-devices, magnetic devices, optics, electronic, magneto-optical, interconnects, membranes, biomedical, photoelectric, thermoelectric devices, ion-conducting electrolytes, batteries, fuel cells, and sensors).

In reference to capacitors, the invention becomes more clear when capacitor fundamentals are considered. The volume effiency of a capacitor is given by the equation $$C/v = (\epsilon_o K)/L^2, \quad (1)$$

where $\epsilon_o$ (=8.85 pF/m) is the permittivity of vacuum, K is the dielectric coefficient, and L is the thickness of the dielectric layer. This expression suggests that the capacitance and volumetric efficiency of ceramic capacitors can be increased if the dielectric layer thickness can be reduced. Thus, reductions in dielectric thickness can lead to ultrathin capacitors with higher volumetric efficiency.

The energy density of a capacitor, E/m, it is given by the equation:

$$E/m = 0.5(CV^2/m) = (\epsilon_o K V^2)/(2\rho L^2), \quad (2)$$

where $\rho$ is the density of the dielectric material, and V is the applied voltage. Again, the relevance of ultra-thin ceramic layer is apparent from the above equation, which suggests that a significant reduction in dielectric thickness can dramatically increase the energy density of the capacitor. Given the fact that nanopowders have powder size that is less than an order of magnitude smaller than conventional precursor powders, the invention offers the potential for improving the performance envelop of capacitors by several orders of magnitude. The unique properties of band-gap engineering and size confinement effects further enhance the service that this invention can provide.

In-reference to varistors, the voltage $V_{1\ mA}$ corresponding to 1 mA current through the varistor is commonly defined as the reference breakdown limit voltage. Varistors are rated for continuous operation at approximately $0.8 \times V_{1\ mA}$. Experimental investigations have established that $V_{1\ mA}$ for varistors can be expressed by:

$$V_{1\ mA} = nL/d_g \quad (3)$$

where n is the nominal voltage drop per interface, L is the thickness of the ceramic layer in the varistor, and $d_g$ is the average size of the grains. It is noted that $V_{1\ mA}$ is independent of the chemical composition and fabrication process of the varistor. Thus, practical ways of increasing the voltage breakdown voltage are: (a) increasing the varistor thickness, and (b) decreasing the grain size. Of these alternatives, present-day processing technology only allows variation in "L," the varistor thickness, while grain size variations are an appealing but commercially unrealizable option. Nanopowders offer the opportunity to reduce the grain size by more than an order of magnitude and therefore can enhance the $V_{1\ mA}$ for a given thickness, or can help miniaturize the varistor, by more than 10 fold for the same voltage surge protection. The invention offers the potential of integrating nanostructured voltage surge layers with active electronic layers and chip. As for capacitors, the size confinement effects further enhance the scope of service that this invention can provide.

With reference to resistors, as would be apparent to those skilled in the art, the resistivity of a material is a function of the mean free path of electrons in the material. More specifically, the resistivity can be derived from the following equation:

$$r = mv_E/(nq^2\lambda) \quad (4)$$

where r is the resistivity, m is the electron mass, $v_E$ is Fermi's energy, n is the number of free electrons per unit volume in the material, q is the electron charge, and $\lambda$ is the electron mean free path. Thus, the resistivity of a material is inversely proportional to the mean free path of electrons in the material. In conventional material formulation used for preparing resistors, the domain size of the material formulation is greater than the mean free path of electrons and therefore resistivity changes can only be accomplished by changes in composition, phase, dopants, temperatures, fields, and voltage. However, if the material's domain size is confined to a size less than the mean free path, as would happen in the case of nanostructured layers, the basic assumption that led to this equation is no longer valid. Therefore, the use of nanosize powders and nanostructured layers with domain size less than the mean free path of electrons is a significant and unique opportunity for preparing unique and commercially useful resistors.

Finally, with reference to inductors, the energy density, E/υ, of a ceramic inductor is given by:

$$E/\upsilon = \frac{1}{2}(L/\upsilon)I^2 \quad (5)$$

where I is the current through the inductive circuit. Combining this with the volumetric efficiency of a ceramic inductor, L/υ, which can be given by:

$$L/\upsilon = \mu_i(4\pi N^2)/C_o \quad (6)$$

where $\mu_i$ is the initial permeability, N is the number of turns, and $C_o$ is the core constant, produces the following equation:

$$E/\upsilon = \frac{1}{2}[\mu_i(4\pi N^2)/C_o]I^2 \quad (5)$$

This expression suggests that the energy density of ceramic inductors can be increased by: (a) increasing the initial permeability of the ceramic; (b) decreasing the core constant; and (c) increasing the current carrying capability of the coil. From a design point of view, the impact of the initial permeability is the most accessible parameter. For example, the energy density of the inductor can be increased by two to four orders of magnitude if the permeability of existing soft magnetic materials can be increased by two to four orders of magnitude. Conventional materials are based on bulk, macroscopic, non-confined properties and the bulk properties values cannot be appreciably engineered. Thus, for inductors - like capacitors, resistors, and varistors - this invention offers materials with properties and performance modified because of domain confinement effects to nanoscale regime. Given the fact that confinement effects can increase resistivities and initial permeabilities, nanostructured layers indeed offer a significant service to inductor users.

Thus, as apparent from the examples of this disclosure, the fundamental breakthrough of the present invention is the preparation of nanostructured layers of ceramics and electrodes and the application of nano-precision engineered powders to passive electronic component manufacturing. According to the preferred embodiment of the invention, as illustrated in FIG. 1, a conducting metal is deposited as an electrode layer 10 on a substrate 12 for mechanical support. The electrode composition can be any metal or alloy, or a composite containing any metal or alloy, with a melting point higher than 900° C., the following being the most preferred: Pt, Pd, Au, Ag, Cu, Ni or alloys thereof. The electrode layer thickness can vary from a few Angstroms to as thick as desired for the particular application and can be deposited by tape casting, screen printing, chemical precipitation, electrochemical techniques, photochemical techniques, sputtering, CVD, PVD, powder metallurgy, or combinations thereof.

Once the electrode has been formed, a film 14 of any desired ceramic material formulation is formed on the electroded surface by one of three ways. According to one method, a well mixed suspension of ceramic nanopowders is prepared and the electroded surface is coated with a ceramic layer from the prepared nanopowder suspension, the resulting film is dried, and the deposition and drying steps are repeated as many times as desired. The suspension medium can be inorganic or organic, but preferably has low viscosity, high density, low vapor pressure, is chemically inert, environmentally benign, and inexpensive. The powders are preferably as small as possible (less than 100 nm), as monodisperse as possible (preferably with standard deviation less than 25 nm), clean at the surface, with minimal surface charge or agglomeration, and spherical. The ceramic nanopowder suspension can be supplemented for property enhancements with additives and for processing ease with binders and aids such as polyethylene glycol and organo-metallic coupling agents. The deposition process can be manual or automatic, forced or gravity assisted, vertical or inclined, linear or rotating (e.g. spin coating), and with substrate stationary and suspension flowing (e.g. printing, casting) or substrate moving and suspension stationary (e.g. dipping), or a combination of these. The drying step can be accomplished by conductive, or convective, or radiative heating, or combination of these, and can be assisted by controlling the composition of the gas environment. It is preferred that the gas environment during heating be such that it does not adversely react or reduce or oxidize the ceramic or electrode layers.

According to a second method, the nanopowders are deposited on the electroded surface by a vapor deposition process. The nanopowders are suspended in flowing gas and impact deposited on the electroded surface. The gas suspension may be heated or charged or accelerated to assist the deposition process. Once the nanopowder has been deposited, it may be pressed. This method does not require the drying step.

A third method is similar to the first one outlined above, the difference being primarily in the fact that in this method a solution of nanostructured precursors is prepared and then the nanopowders are precipitated directly onto the electrode surface. After the nanopowders have been deposited from the solution, the same steps of the first method are followed.

Once the ceramic layer 14 has been deposited, it is densified by sintering. The sintering step is accomplished at moderate temperatures (positively less than 1500° C., preferably below 950° C.) through a thermal profile over a time period. The heating can be accomplished by conductive, convective, or radiative heating, or a combination of these. The sintering step can be assisted by controlling the composition of the gas environment. It is preferred that the gas environment during heating be such that it does not react or reduce or oxidize the ceramic or electrode layers in a manner that adversely affects the component's performance. However, the gas environment may be controlled such that it reacts or reduces or oxidizes the ceramic or electrode layers in a manner that favorably affects the component's performance. The sintering time is kept to a minimum to minimize grain growth that naturally occurs at higher temperatures. Note that the sintering temperature determines the metal or alloy that can be used for the particular application, any temperature (such as less that 1,000° C.) lower than the temperatures currently required being a significant advantage over the prior art. Once the ceramic layer 14 has been densified by sintering, another layer 10 of electrode is similarly deposited on the exposed surface of the ceramic layer to produce a nanostructured single layer component.

Multilayer components can be formed in two different ways. In a first method, the steps of electrode layer deposition, ceramic layer deposition, ceramic layer drying, and ceramic layer sintering are repeated alternatively until the desired number of layers has been formed. In a second method, which is preferred, the steps of electrode layer deposition, ceramic layer deposition, and ceramic layer drying are repeated until the desired layers have been formed and then the sintering step is executed to densify all the ceramic layers. It is noted that the later method of preparing multilayer component is advantageously carried out faster and with less energy requirement.

It is also noted that this invention enables the sintering step to be carried out at lower temperatures and faster than the corresponding step of prior-art methods and at temperatures as low as 850° C. because of the much greater diffusivity of nanosize particles in comparison to conventionally used materials, as mentioned above. Therefore, production savings result from lower operating temperatures, which require less energy input and less equipment insulation. Most importantly and advantageously, the lower sintering temperature permits the use of electrode compositions with lower melting points, such as those containing larger concentrations of silver or even pure silver, which is less expensive and a better conductor than the metals and alloys (e.g., of Pd and Pt) heretofore used as a result of the high temperature requirements of the sintering step of prior-art processes.

Finally, it is noted that the process of the invention can be readily used to prepare arrays of passive components—that is, devices with multiple passive components codeposited in series or parallel of each other in a single package.

The following examples illustrate how the invention was reduced to practice.

Figure 2:
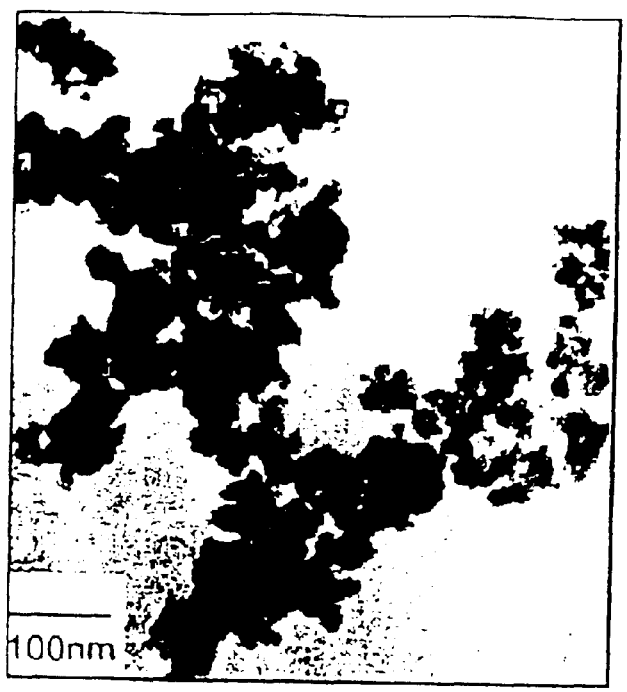
FIG. 2 is a transmission electron microscope image of the powder used in Example 1.
Figure 3:
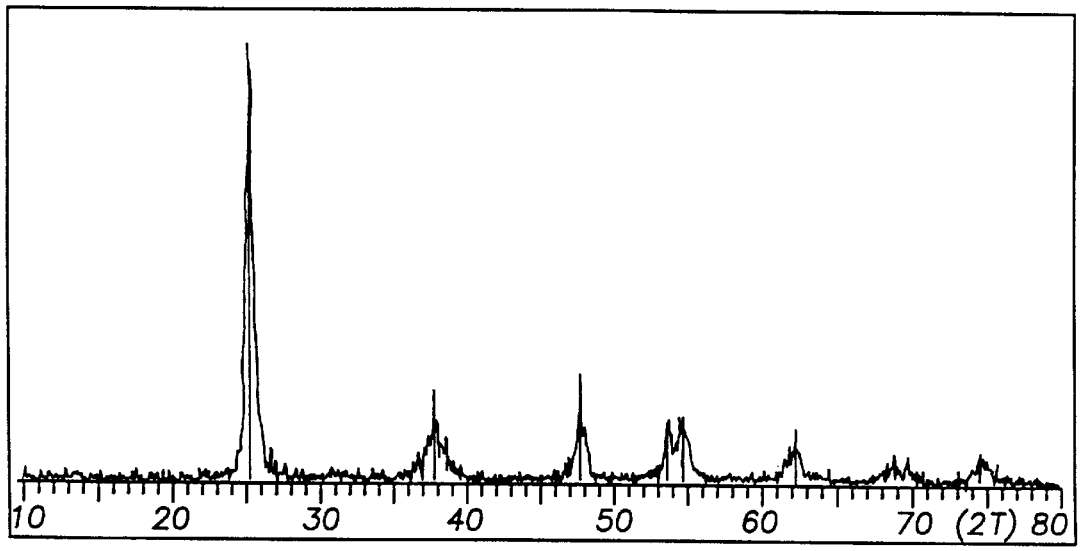
FIG. 3 is an X-ray diffraction pattern of the $TiO_2$ powder used to form the dielectric layer of Example 1.

EXAMPLE 1—Capacitor $TiO_2$ nanopowders were synthesized by chemical precipitation of $TiCl_4$. The aqueous chloride solution was cooled and maintained at 0° C. and precipitated by adding 7M $NH_4OH$ under rapid stirring. The precipitates were then filtered and calcined in air for one hour at 400° C. The nanopowders produced were characterized using TEM, XRD, and BET adsorption equipment. FIGS. 2 and 3 are a TEM image and an XRD spectrum, respectively, of the nanopowders. The mean size of the nanopowder, as determined by TEM was 13.9 nm, with a standard deviation, as determined by TEM, of 4.4 nm. The phase, as determined by XRD, was found to be anatase TiO2; and the surface area as determined by BET was 66.7 m2/gm. The nanopowders were suspended in denatured alcohol with 1 wt % polyethylene glycol binder for preparing the dielectric layer.

Single crystal Si wafers (½"×½") were used as substrates for mechanical support. The substrate was first coated with a thin layer of Pd/Ag alloy (about 500 nm in thickness) using plasma sputtering, and then coated with a thin film of $TiO_2$ as follows.

The nanopowder suspension in denatured alcohol was stirred and then the substrate was dipped into the suspension and removed. The uniform ultra-thin $TiO_2$ film on the Si substrate was dried and sintered in air. The drying was first done in air at room temperature for 30 minutes and then in a furnace at 150° C. for 30 minutes. The densification was done in the furnace at 850° C. for 2 hours. The resulting surface of the $TiO_2$ layer was further coated with a Pd/Ag layer (about 500 nm in thickess and 5 mm in diameter) to produce an ultra-thin $TiO_2$ capacitor on a silicon substrate.

Figure 4A:
FIG. 4($a$) is a scanning electron microscope image of the cross section of a coated substrate obtained in Example 1, showing a substrate layer covered by uniform layers of a metallic electrode and dielectric material.
Figure 4B:

In order to characterize the $TiO_2$ coated substrate, the wafers were fractured and their cross sections were observed under a Hitachi field emission scanning electron microscope (SEM model S-4500). The samples were not coated with conductive Au during SEM in order to avoid any possible cover-up of nanostructure details by coated Au films. FIG. 4(*a*) shows (at 25,000×magnification) the thickness and uniformity of the cross section of a $TiO_2$ coated substrate; the white layer is a Pd/Ag film (the electrode) of about 500 nm in thickness on a Si substrate. The $TiO_2$ film in this case was about 850 nm in thickness. The microstructure of the $TiO_2$ film is shown in FIG. 4(*b*) at 10,000×magnification; the average grain size of $TiO_2$ was as small as 100 nm.

The dielectric properties of these ultrathin dielectric capacitors were evaluated using an HP 4274A Multifrequency LCR meter, a Ransco Thermal Cycler (for capacitance measurements), and a Keithley 246 high voltage supply (for breakdown voltage measurements). The capacitance measurements were conducted at different temperatures from 30° C. to 130° C. with a frequency of 1 kHz. The dielectric constant so determined was 89.2. The dissipation factor was less than 5%, while the dielectric strength of the nanostructured layer was observed to be 220 Volts/micrometer. The temperature coefficient of capacitance was found to be less than 1%. Compared to a micron powder based 20 micron dielectric layer capacitor, the capacitor prepared from nanoscale, interface confined powders was found to enhance volumetric efficiency by 100 fold, and energy density by more than 2000 fold.

Nanostructured dielectric layer capacitors prepared from directly precipitating nanostructured layer on silicon wafer from a solution of titanium alkoxides in a moist environment using spin coating apparatus also exhibited statistically similar performance.

Nanostructured capacitors prepared from nanopowders produced by other processes, such as the method disclosed in the referenced copending applications, exhibited statistically similar performance, as illustrated below.

EXAMPLE 2—Capacitor

Single crystal Si wafers (½"×½") were again used as substrates for mechanical support. The substrate was first coated with a thin layer of Pd (about 500 nm in thickness) using plasma sputtering, and then coated with a thin film of $TiO_2$ as follows.

Figure 5:
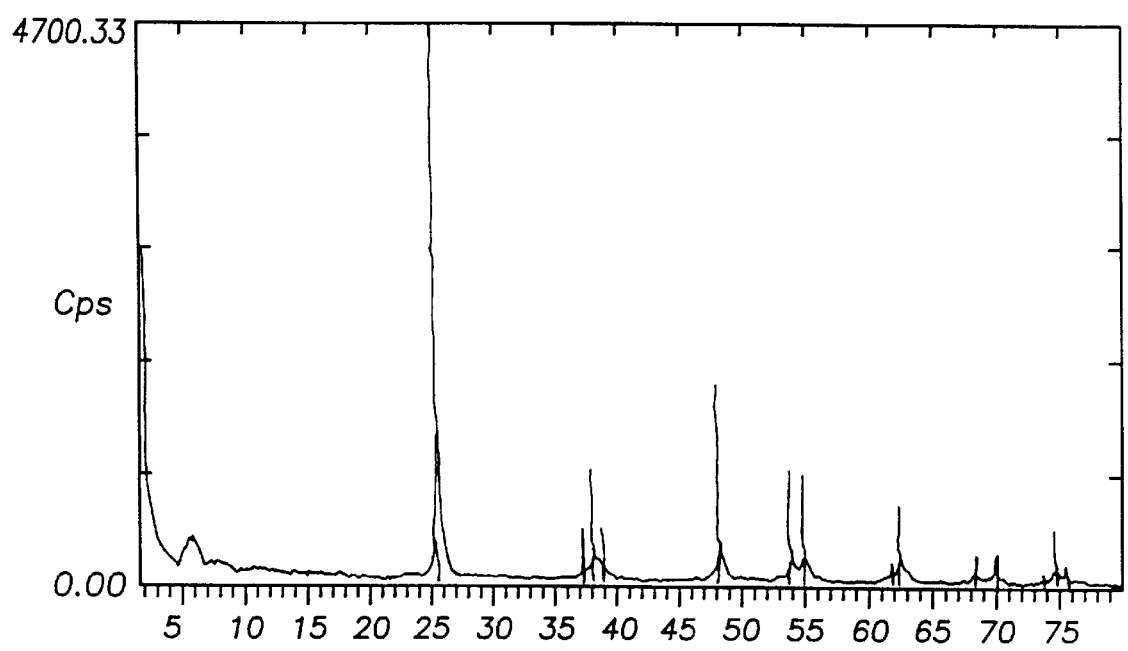
FIG. 5 is an X-ray diffraction pattern of the $TiO_2$ powder used to form the dielectric layer of Example 2.
Figure 6:
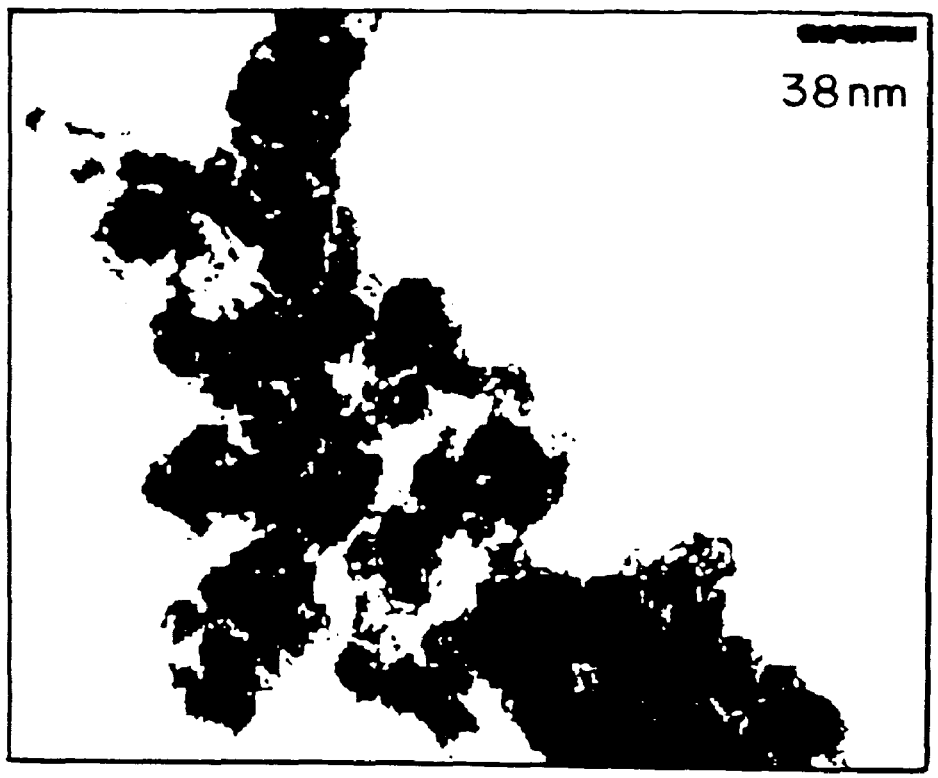
FIG. 6 is a transmission electron microscope image of the powder used in Example 2.

A suspension was made from nano-$TiO_2$ powder with average grain diameter of 20 nm and a standard deviation of about 2.8. FIG. 5 is an XRD pattern and FIG. 6 is a TEM image of the nanoscale dielectric powder. A polyethylene glycol binder and ethanol solvent were used. The suspension was stirred for 24 hours before coating. The dip coating method was used to prepare uniform ultra-thin $TiO_2$ films on the Si substrates. The film was dried and sintered in air. The drying was first done in air at room temperature for 30 minutes and then in a furnace at 150° C. for 30 minutes. The densification was done in the furnace at 850° C. for 2 hours. The resulting surface of the $TiO_2$ layer was further coated with a Pd layer (about 500 nm in thickess and 5 mm in diameter) to produce an ultra-thin $TiO_2$ capacitor on a silicon substrate.

Figure 7A:
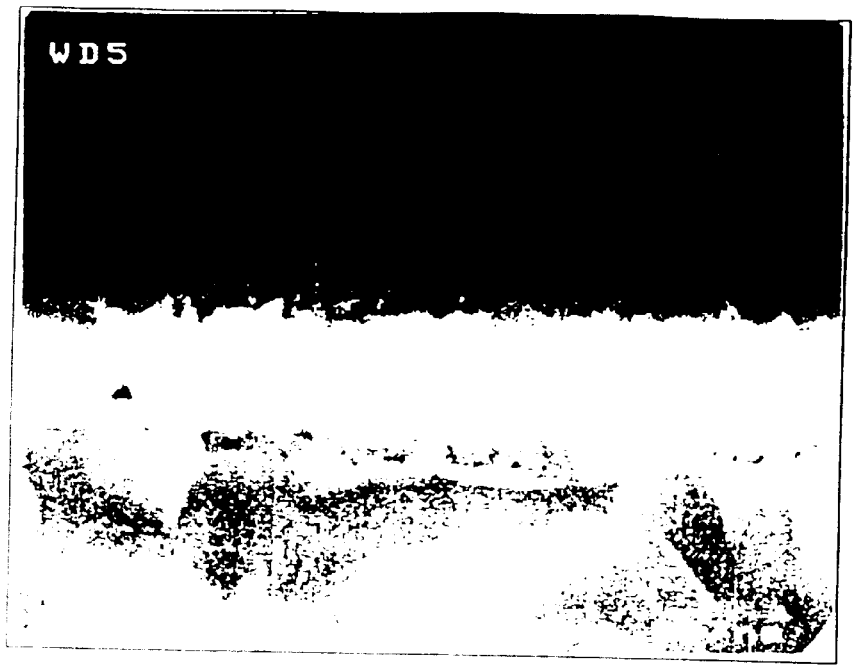
FIG. 7($a$) is a scanning electron microscope image of the cross section of a coated substrate obtained in Example 2, showing a substrate layer covered by uniform layers of a metallic electrode and dielectric material.
Figure 7B:

In order to characterize the $TiO_2$ coated substrate, the wafers were fractured and their cross sections were observed under a Hitachi field emission scanning electron microscope (SEM model S-4500). The samples were again not coated with conductive Au during SEM in order to avoid any possible cover-up of nanostructure details by coated Au films. FIG. 7(*a*) shows (at 25,000×magnification) the thickness and uniformity of the cross section of a $TiO_2$ coated substrate; the white layer is a Pd film (the electrode) of about 500 nm in thickness on a Si substrate. The $TiO_2$ film in this case was about 850 nm in thickness. The microstructure of the $TiO_2$ film is shown in FIG. 7(*b*) at 100,000× magnification; the average grain size of $TiO_2$ was as small as 100 nm.

Figure 8:
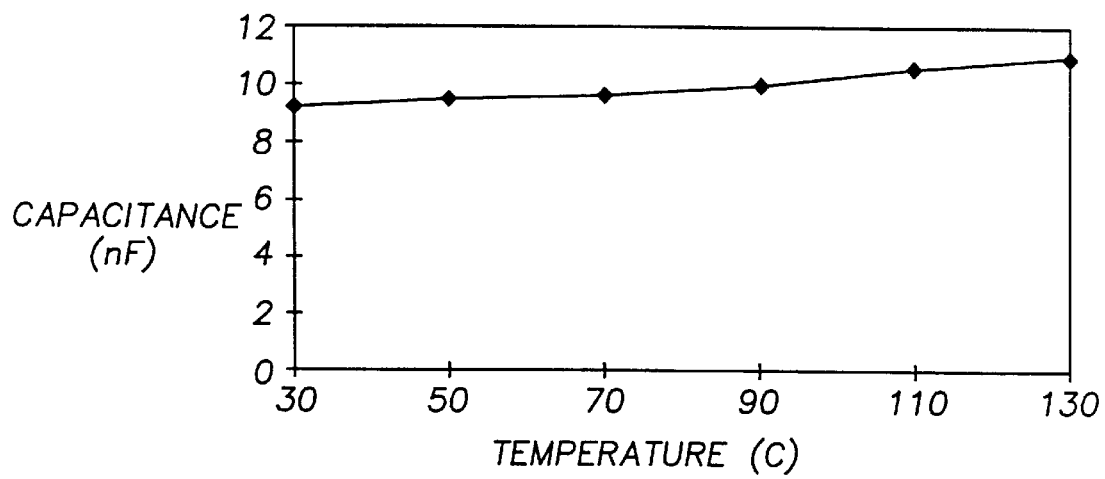
FIG. 8 is a graph of the capacitance vs. temperature characteristics of a typical $TiO_2$ capacitor manufactured according to the process of the invention.

The dielectric properties of these ultrathin dielectric capacitors were also evaluated using an HP 4274A Multifrequency LCR meter, a Ransco Thermal Cycler (for capacitance measurements), and a Keithley 246 High Voltage Supply (for breakdown voltage measurements). The capacitance measurements were conducted at different temperatures from 30° C. to 130° C. with a frequency of 1 kHz. The measured dielectric properties of this ultra-thin TiO$_2$ capacitor are listed in Table 1 below. A graph of the capacitance vs. temperature is shown in FIG. 8.

TABLE 1

| | |
|---|---|
| Dielectric Thickness ($\mu$m) | 1.67 $\mu$m |
| Electrode area (mm$^2$) | 19.625 |
| Capacitance @ 25° C. (nF) | 9.28 |
| Dielectric Constant @ 25° C. | 89.2 |
| Dissipation factor (%) | 5.0 |
| Dielectric Strength (V/$\mu$m) | 220 |

The volumetric efficiencies of base capacitors (20 and 100 $\mu$m in thickness) and of ultra-thin TiO$_2$ capacitors (2 $\mu$m in thickness) were calculated for comparison according to equation (1). The results are listed in Table 2 below.

TABLE 2

| Capacitors | Base case L = 100 $\mu$m | Base case L = 20 $\mu$m | Nanoceramic L = 2 $\mu$m |
|---|---|---|---|
| C/v (nF/cm$^3$) | 0.078 | 1.77 | 177 |

The data in Table 2 show that, compared to the base case where the thickness was 20 $\mu$m, the nanostructured TiO$_2$ capacitor enhanced the volumetric efficiency by 100 times. Compared to the base case where the thickness was 100 $\mu$m, the nanostructured TiO$_2$ capacitor enhanced the volumetric efficiency by over 2,200 times.

The energy densities of base capacitors (20 and 100 $\mu$m in thickness) and nanostructured TiO$_2$ capacitors (2 $\mu$m in thickness) were also calculated according to equation (2). The calculated results are listed in Table 3 which shows that, compared to the base case where the thickness is 20 $\mu$m, a nanostructured TiO$_2$ capacitor 2 $\mu$m thick would raise the energy density of the dielectric layer by 100 times. Compared to the base case where the thickness is 100 $\mu$m, the nanostructured TiO$_2$ capacitor would raise the energy density of the dielectric layer by about 2,500 times.

TABLE 3

| Capacitors | Base case L = 100 $\mu$m | Base case L = 20 $\mu$m | Nanoceramic L = 2 $\mu$m |
|---|---|---|---|
| E/m (J/kg) | 2.13 × 10$^{-2}$ | 5.32 × 10$^{-1}$ | 53.2 |
| E/m (w.hr/kg) | 5.92 × 10$^{-6}$ | 1.48 × 10$^{-4}$ | 1.48 × 10$^{-2}$ |

These examples demonstrate that capacitors can be prepared from dielectric powders with mean size less than 100 nanometers resulting in capacitor dielectric layers with post-densification grain size of less than 1 micron. The examples also illustrate a procedure for preparing micron and submicron layers of electrical and electronic ceramics sandwiched between electrically conducting electrodes and for preparing ceramic capacitors at processing temperatures low enough that pure silver can be used as the electrode material instead of expensive alloys of silver.

While silver alone was not used as electrode material because of availability, the low sintering temperature of 850° C. supports the premise that silver can be used as electrode for nanostructured layer capacitors.

Figure 9:
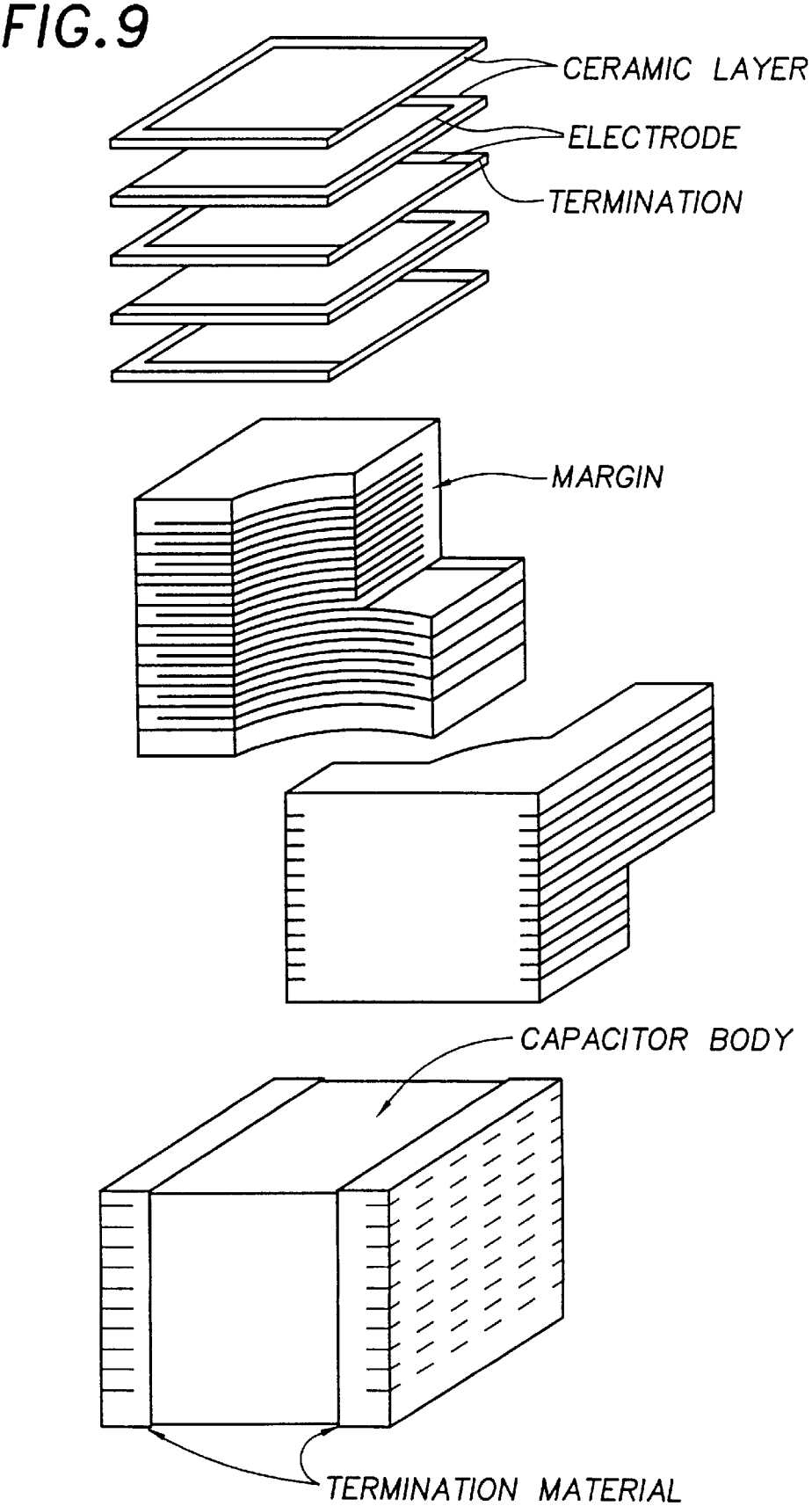
FIG. 9 is a schematic illustration of a multilayer ceramic capacitor structure manufacture according to the process of the invention.
Figure 10:
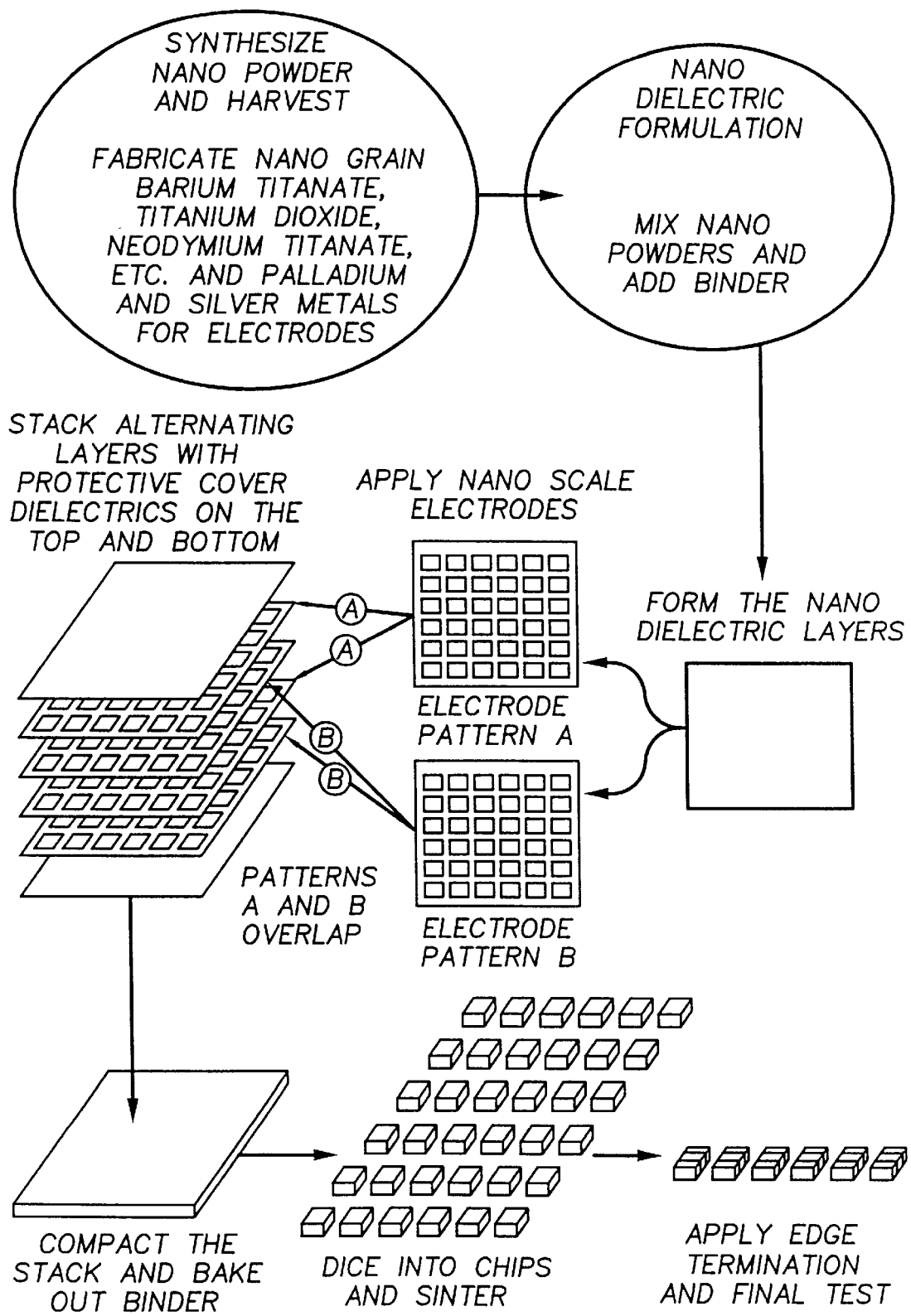
FIG. 10 is an illustrated schematic process flow for nano-layered ceramic capacitors manufactured according to the invention.
Figure 11:
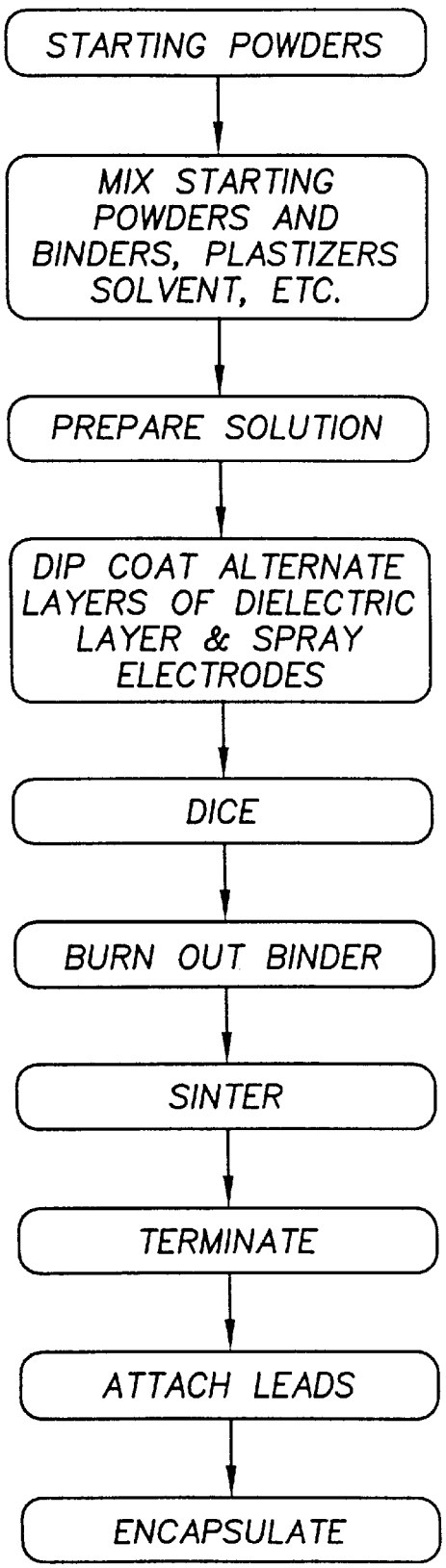
FIG. 11 is a flow diagram for the fabrication process of FIG. 11.

Based on these results, it is anticipated that multilayer ceramic capacitors can be similarly fabricated to produce the structure 30 illustrated in FIG. 9. Ultra-thin (about 400 nm) dielectric layers 32 can be packed into the minimum possible space in a mechanically robust form. The typical interelectrode spacing can be about 400 nm, which is more than 25 times thinner than what the best current technology can achieve. Thus, 50 to 100 layers can be stacked in a small volume. As illustrated in the schematic representation of FIG. 10 and the flow chart of FIG. 11, the process involves the following major steps: preparing the ceramic solution, making ultra-thin layers, preparing electrodes, dicing into chips, firing (densification), making terminations and testing.

Thus, the invention demonstrated that very high energy density and very high power density multilayered capacitors can be fabricated from nanostructured ceramic dielectrics, i.e., monosize ceramic dielectric powders with mean particle size in the 10$^{-1}$ to 10$^{-3}$ $\mu$m range. Through the use of nanoceramics, the invention achieved a reduction of the dielectric layer thickness by more than an order of magnitude, thereby providing a commensurate degree of miniaturization and enhancing the capacitance and energy density of same size multilayered capacitors by a factor of up to 10$^6$. It showed the possibility of dramatically lowering the ESR of multilayered capacitors, with consequent increase in power density by several orders of magnitude. Although experimental data suggest that the dielectric constant of materials first decreases as the grain size becomes smaller, the use of nanostructured materials confirmed the fact that beyond a critical diameter (smaller than 1 $\mu$m) the dielectric properties enter a different phenomenological regime and reductions in grain size significantly enhance the dielectric constant. Nanoceramics are superplastic (very ductile) at relatively moderate temperatures and therefore can produce ultra-thin plates of dielectric more easily and without the use of binders, which reduces impurity contamination. The enhanced creep rates in nanoceramics can allow for low temperature (less than 950° C.) sintering of the nanostructured film to produce a defect-free, full density dielectric layers. An additional advantage of the low-temperature sintering characteristics of nanoceramics is the replacement of expensive Ag/Pd alloys with Ag as the electrode layer material. Moreover, experimental data suggest that nanoceramics are stronger and harder, by more than 500%, than bulk ceramics, which implies that nanostructured capacitors would be mechanically robust even after reduction of the dielectric layers' thickness. Nanoceramics, because of their nanoscale sizes, can lead to a homogeneous mixing of K-modifiers and additives to near-theoretical levels. This should enable the creation of multilayered capacitors and other passive electronic components with very low performance spread. Inasmuch as it has been suggested that nanostructured ceramics should feature a lower coefficient of thermal expansion than their larger precursors, the temperature coefficient of nanostructure components should be lower than that of existing components. Similarly, the lower temperature coefficient of capacitance of nanostructured capacitors should enable their use in applications requiring a broader temperature range (e.g., for dual-use applications such as hybrid or electric vehicles where under-hood temperatures can reach 150° C.). Finally, based on the observation that some nanoceramics have unique electronic properties [Eastman et al., "Processing and Properties of Nanophase Oxides," Mater Res. Soc. Symp. Proc., 155, 255 (1989)], it is expected that the performance of passive electronic components can be improved for operation at higher frequencies and that nanostructured components may be engineered with unique combinations of properties that have been heretofore unavailable.

From a commercial point of view, the approach of this invention is also very desirable because it does not require novel chemistries or components whose environmental and ecological impact is unknown. The approach also avoids the pit-fall common to competitive technologies that ignore raw material availability and source issues, scale up issues, manufacturing equipment availability, and labor training issues. Powder processing has been practiced by the passive component industry for decades. Therefore, the approach of this invention blends well with current reality and builds on it by exploring, developing and implementing the knowledge of precision engineering to the art. Nanopowders, therefore, are an extraordinary opportunity for design, development and commercialization of a wide range of structural, electrochemical, electrical, optical, electronics, magnetic and chemical applications. Furthermore, since nanopowders represent a whole new family of precision engineered material precursors where conventional coarse-grain physiochemical mechanisms are not applicable, nanomaterials offer unique combinations of properties that may enable novel and multifunctional components of unmatcbed performance.

EXAMPLE 3—Varistors

Figure 12:
FIG. 12 is a transmission electron microscope image of the ZnO powder used in Example 3.
Figure 13:
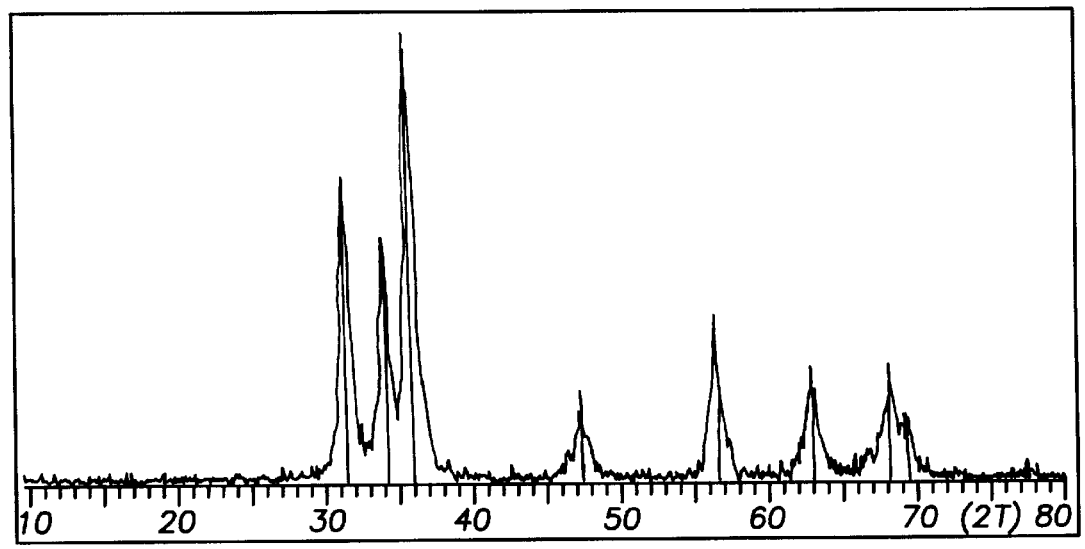
FIG. 13 is an X-ray diffraction pattern of the ZnO powder used to form the ceramic layer of Example 3.

Nanoscale powders of zinc oxide were obtained as follows in order to manufacture varistors according to the invention. Zinc carbonate was precipitated by mixing solutions of zinc nitrate and ammonium carbonate in equal molar ratio. Specifically, a 0.1 molar solution of $Zn(NO_3)_2$ was prepared by dissolving 29.747 g of the salt in distilled water. Approximately 0.1M $(NH_4)_2CO_3$ was prepared by dissolving 11.34 g of ammoniun carbonate (assay $\geq 30\%$) in distilled water. On hundred ml of 0.1M $Zn(NO_3)_2$ solution was added slowly into a stirred solution of 100 ml of 0.1M $(NH_4)2CO_3$. Precipitation occured immediately. After stirring for more than one half hour, the precipitate was filtered using a buchner funnel fitted with a fritted disc (ASTM 10–15 $\mu$m) by vacuum suction. The precipitate was washed with water twice and then washed with ethanol. The precipitate was dried in air and then at 70° C. The powder obtained was ground thoroughly using agate or alumina mortar and pestle and calcined between 200 and 300° C. for 2 hours. The calcined powder was characterized by XRD, TEM and BET adsorption. FIGS. 12 and 13 are the TEM image and the XRD spectrum, respectively, of the nanopowder produced and used in this example. The powder was nanoscale ZnO with typical sizes in the range of 5 to 20 nm. The mean size of the nanopowder, as determined by TEM, was found to be 11.2 nm with a standard deviation of 3.4 nm; the phase, as determined by XRD, was hexagonal ZnO, and the surface area as determined by BET was 55.8 m2/gm. The nanopowders were suspended in denatured alcohol.

According to the invention, nanoscale $Sb_2O_3$ (1 wt %), $Bi(NO_3)_3 \cdot 5H_2O$ (1 wt %), $Ni(NO_3)_2 \cdot 6H_2O$ (1 wt %), $Co(NO_3)_2 \cdot 6H_2O$ (0.5 wt %), $Mn(NO_3)_2 \cdot xH2O$ (0.5 wt %), $Al(NO_3)_3 \cdot 9H_2O$ (0.001 wt %) and $Cr(NO_3)_3 \cdot 9H_2O$ (0.1 wt %) were mixed with nanoscale ZnO powders (95.9 wt %) and reacted at 400° C. for 0.5 hours, and then at 300° C. for 1.5 h. The nanocomposite powders were uniaxially pressed in a steel die at 20,000–30,000 psi. The discs were sintered in air at various temperatures for 1 to 2 hours. Sintered discs were given electrical contacts by printing silver paste on the opposite faces of the pellets. Platinum lead wires were attached to the silver paste. The silver paste was then dried by heating in an air oven at 80–100° C. for 1 hour.

Figure 14:
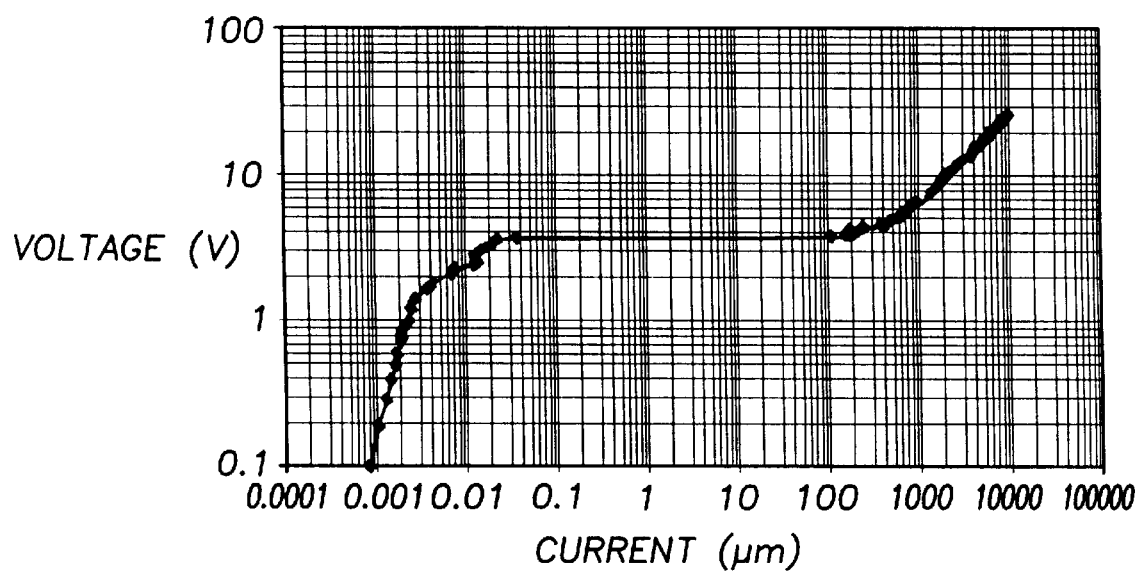
FIG. 14 is a voltage-current plot of the behavior of the varistor manufactured according to the invention in Example 3.

Varistors so obtained were characterized for voltage-current behavior using a Keithley 2400 Source Meter. The resulting plot is shown in FIG. 14. The nominal breakdown voltage (Vnom) and alpha ($\alpha$) were determined from the data so obtained from the equation:

$$\alpha = \log(I_2/I_1)/\log(V_2/V_1)$$

where $V_1$ and $V_2$ are the voltages across the varistor at two test currents $I_1$ and $I_2$ in the non-linear region of the V-I characteristic. The nominal varistor (or breakdown) voltage, Vnom, is the varistor peak terminal voltage measured with a specified DC current applied (normally 1 mA for a corresponding varistor terminal voltage $V_{1\,mA}$.

For varistors discs that were sintered at 850° C. for one hour, an $\alpha$ of 19.5 and a $V_{nom}$ of 429 V/mm (at I=0.1 mA/cm$^2$ ) were observed. For varistor discs that were sintered at 1200° C. for one hour, an $\alpha$ of 30 and a $V_{nom}$ of 23 V/mm (at =1.9 mA/cm$^2$) were observed.

EXAMPLE 4—Resistors

Figure 15:
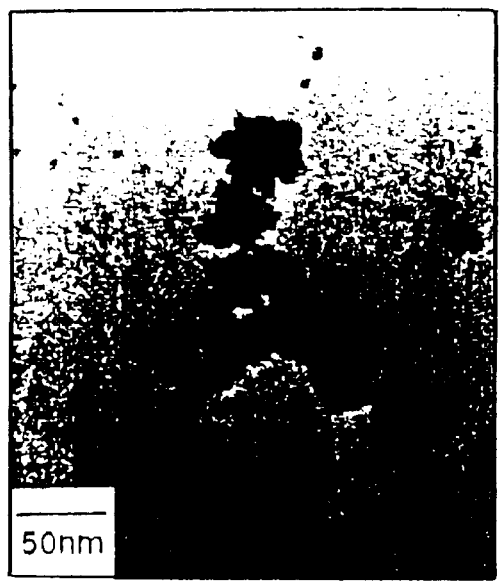
FIG. 15 is a transmission electron microscope image of the $SnO_2$ powder used in Example 4.
Figure 16:
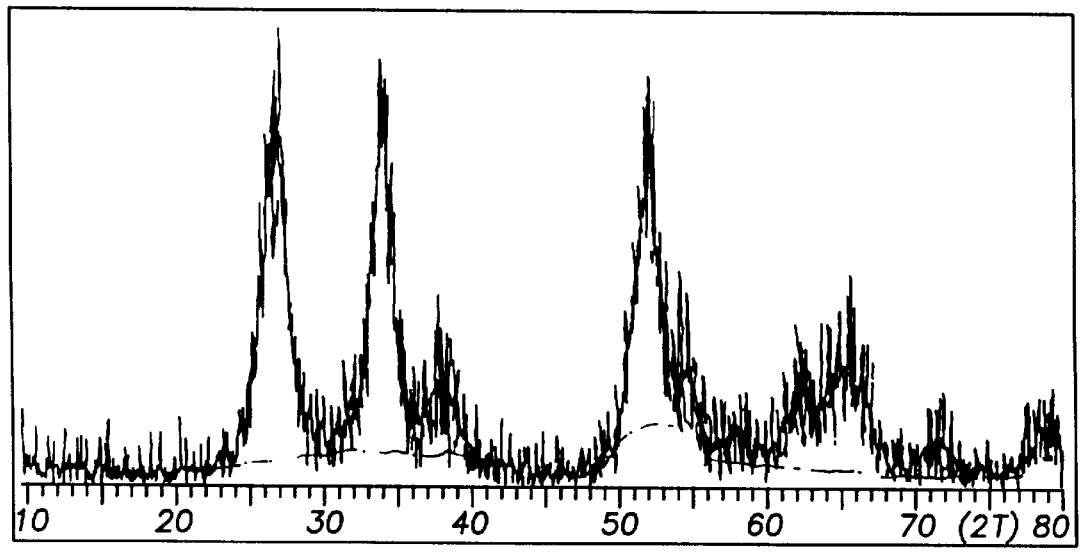
FIG. 16 is an X-ray diffraction pattern of the $SnO_2$ powder used to form the ceramic layer of Example 4.

Resistors were prepared according to the invention from nanoscale SnO2 powders. An 85% $SnCl_4$ (wt %) aqueous solution was kept at 0° C. and precipitated by adding 14% $NH_4OH$ (wt %) with rapid stirring. The precipitate was filtered and washed with deionized water at 0° C. The powder was then dried at 100° C. for 60 minutes, ground, and calcined at 500° C. for 15 minutes. The nanopowder produced was characterized using TEM, XRD, and BET adsorption equipment. FIG. 15 is the TEM image and FIG. 16 is the XRD spectrum of the nanopowder. The Scherrer's grain size estimated from peak broadening of the XRD data was 4.1 nm. The specific surface area obtained from BET measurement was 97.7 m$^2$/g. The TEM micrograph indicated that the particle size and distribution were 9.1 nm with a standard deviation was 6 nm, and that the particle shape was round and irregular. EDS data showed strong Sn peaks and no other impurity.

A resistor was prepared from the nanopowder as follows. A high-temperature C4740S silver conductor paste (from Heracus Inc. of West Conshohocken, Pa.) was used to fabricate the electrode. The silver paste was painted on an alumina substrate, and air-dried for 15 minutes at 150° C.; the element was then stabilized at 850° C. for 10 minutes to provide conducting electrode layers that strongly adhered to the substrate. Nanosized Sno$_2$ was suspended in ethanol and dried to form a paste. The nanopowder paste was painted between electrodes. After air-drying, the binder solution (a silicate solution with a volume ratio of tetraethyl orthosilicate/ethanol/water/2%HCI of 65/27/7/1) was painted on the SnO$_2$ layer and allowed to permeate the SnO$_2$ layer. The element was air-dried and sintered at 450° C. for 30 min.

Figure 17:
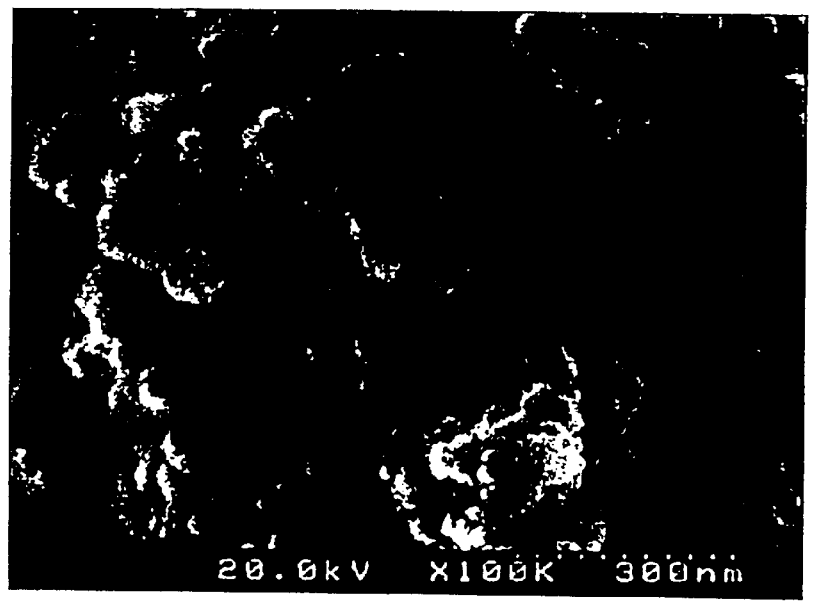
FIG. 17 is a scanning electron microscope image of the $SnO_2$ ceramic film produced in Example 4.
Figure 18:
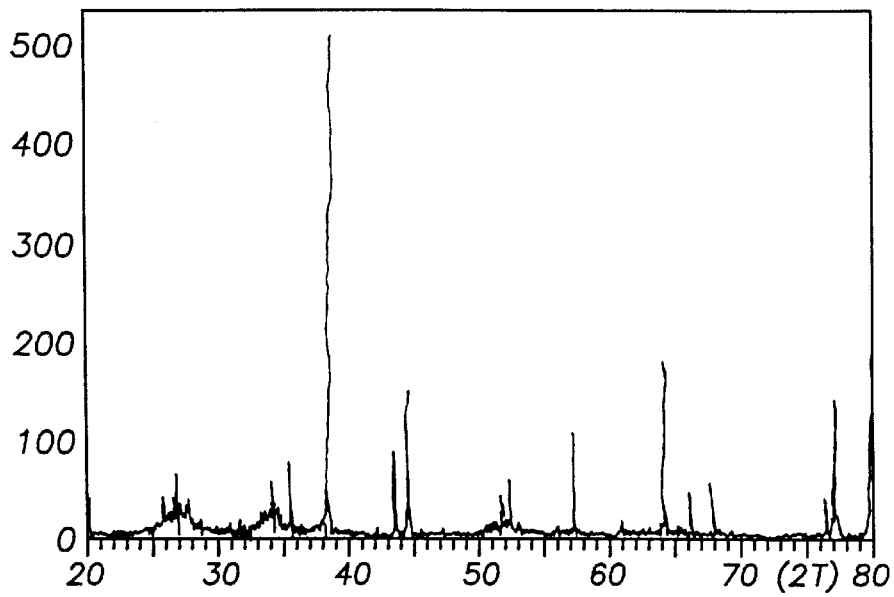
FIG. 18 is an X-ray diffraction pattern of the $SnO_2$ film produced in Example 4.

The nanostructured SnO$_2$ ceramic film was characterized by scanning electron microscopy and XRD, shown in FIGS. 17 and 18, respectively. The XRD data confirmed the phase and the fact that the ceramic film was SnO$_2$. The Scherrer's post-sintering grain size was estimated from peak broadening of the XRD data to be 4.9 nm. The SEM image of the nanostructured SnO$_2$ film indicated that the microstructure of the film was extremely porous, that feature size of the SnO2 cluster was about 20–30 nm, and that each of the SnO2 clusters consisted of several extremely fine SnO2 particles.

Figure 19:
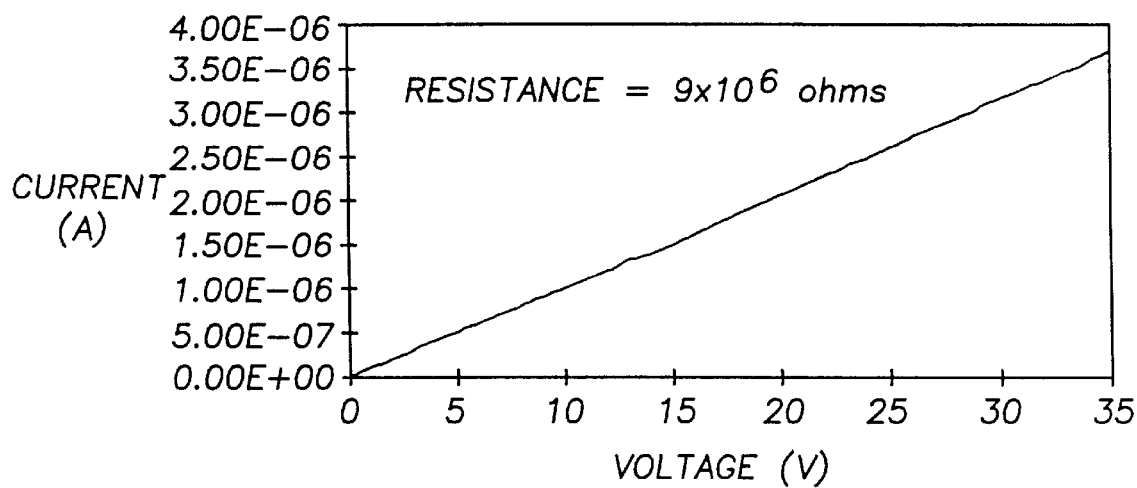
FIG. 19 is a plot of the voltage-current behavior for a typical thin film resitor manufactured according to the invention in Example 4.

A Keithley model 2400 SourceMeter was us ed to determine the electrical behavior of synthesized SnO$_2$ thin films. Using a software application developed with Test Point 2.0, a standard characterization routine was performed for thin resistor film prototypes. Four-point probe leads were attached to each of the silver-painted electrodes, and the circuit was tested by measuring the film resistance at 21 volts (dc). Using the Test Point application Software, a voltage ramp of 0 to 35 volts (DC) was programmed to execute with a step size of 0.5 volts. The current through the film was measured at each voltage step and data were sent to a Microsoft Excel spreadsheet. The resulting current and voltage data were plotted against each other, and the slope of the line was used to calculate the resistance of each thin film using Ohm's law R=V/I. A plot of the V-I behavior for a typical thin film sample is illustrated in FIG. 19, showing a linear relationship and a calculated dc resistance of about 9 megaohms. Background scans of the alumina substrate were also performed to ensure that all resistance effects noted were from the $SnO_2$ film. AC impedance measurements of $SnO_2$ films were performed with a Solartron 1250 impedance/gain analyzer and Z60W analysis software. Probe lines were connected to the silver electrodes of the $SnO_2$ films and an AC resistance of 10 megaohm was observed at a frequency of 1000 Hz.

EXAMPLE 5—Inductors

Figure 22:
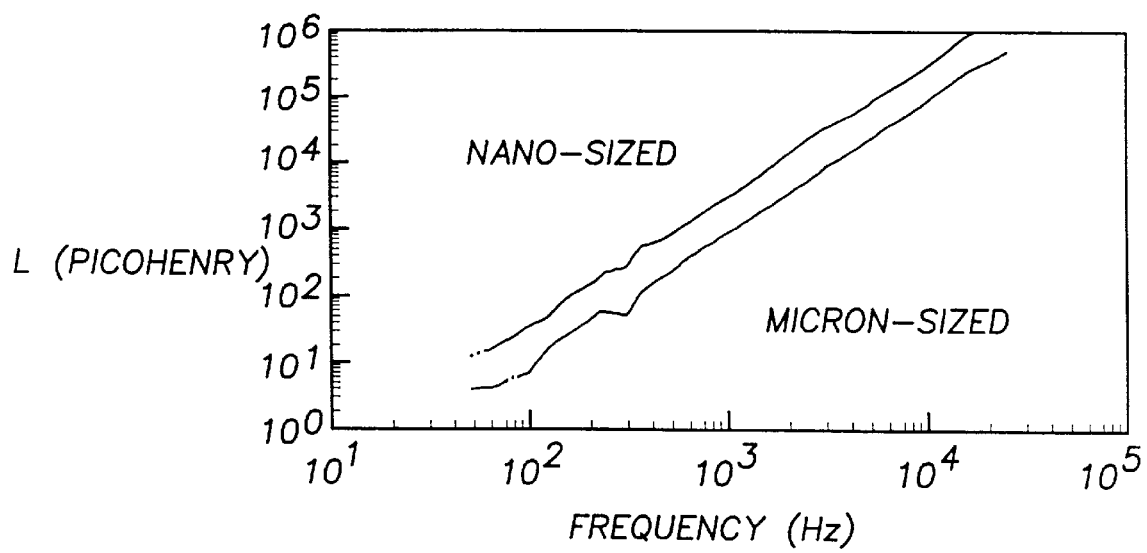
FIG. 22 is an inductance vs. frequency plot illustrating the order-of-magnitude improvements in performance of inductors obtained by nanostructured engineering.
Figure 21:
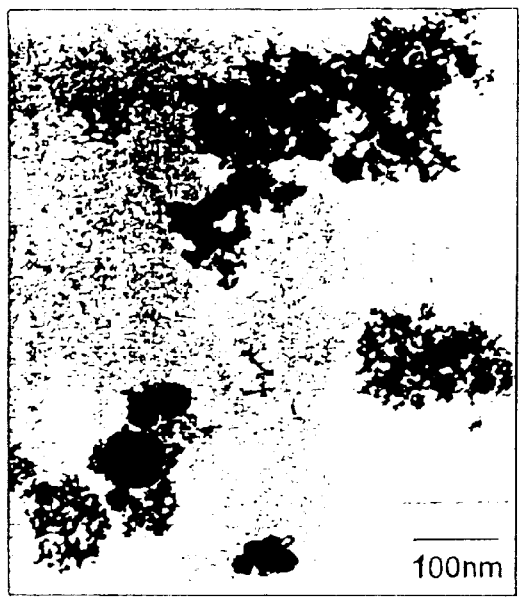
FIG. 21 is a TEM image of the ferrite powder used in Example 5.
Figure 20:
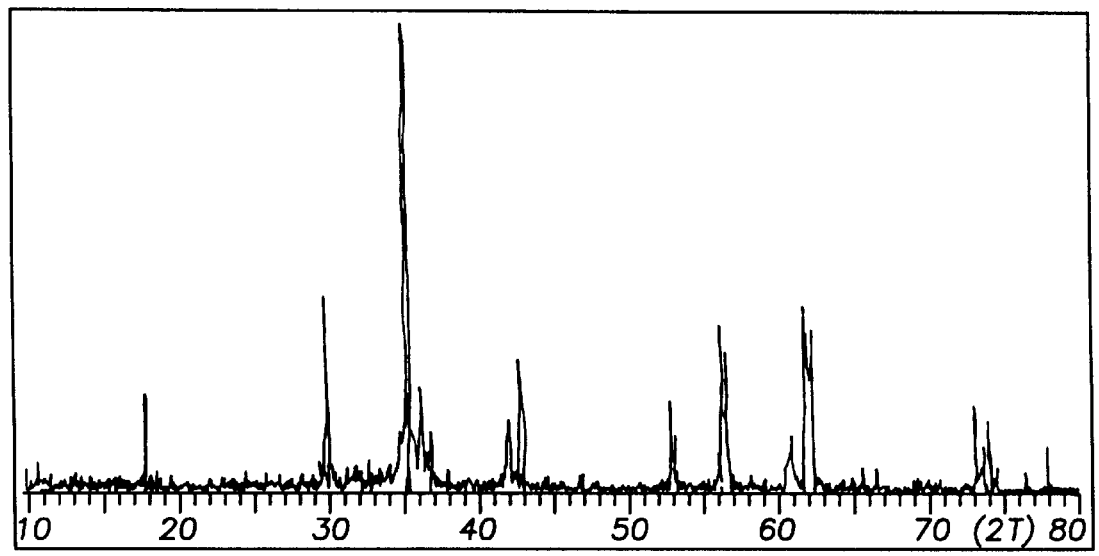
FIG. 20 is an X-ray diffraction pattern of the ferrite powder used to form the ceramic layer of Example 5.

Inductors were made according to the invention from nanoscale ferrite and from micron-sized particles for comparison purposes. The nanopowders were produced by the thermal quench process disclosed in the referenced copending applications and had an average grain size of 45 nm, a standard deviation of 17.1 nm, and a surface area of 25.1 $m^2/g$, as determined by the XRD, TEM and BET adsorption data shown in FIGS. 20 and 21. The nanopowders so produced and conventional ferrite powders (for comparison purposes) were pressed into cylinders (diameter=0.5 cm and length=1 cm) by mixing 1.5 g of ferrite ($NiFe_2O_4$) with 5 wt % of acrylate binder and dispersing the mixture into a solvent ($EtOH:H_2O=1:1$-Vol.:Vol.). The mixture was then sonicated for 30 minutes and the solvent was allowed to evaporate in an oven. When the powders were completely dry, they were pressed into cylinders with a Carver hydraulic press at 90,000 psi. The nanopowder-based cylinders were then sintered at 820° C. for 4 hrs. Note that micron powders of ferrite could not be sintered at this temperature, but required sintering at 1200° C. for 4 hrs. The inductor was prepared by wrapping silver wire (diameter 0.5 mm) in a spiral fashion around the ferrite cylinders (inductor cores). The coil had 50 turns and a diameter of 5.66 mm for both the micron powder based inductor core and for the nanopowder based inductor core. The inductance of the samples was then measured from 30 Hz to 30000 Hz using a computer interfaced Solartron 1260 (Frequency/Gain-Phase Analyzer). The results, shown in FIG. 22, indicate that the inductance of nanopowder-based cores is almost an order of magnitude higher than that of cores based on conventional micron-sized powders.

Figure 23:
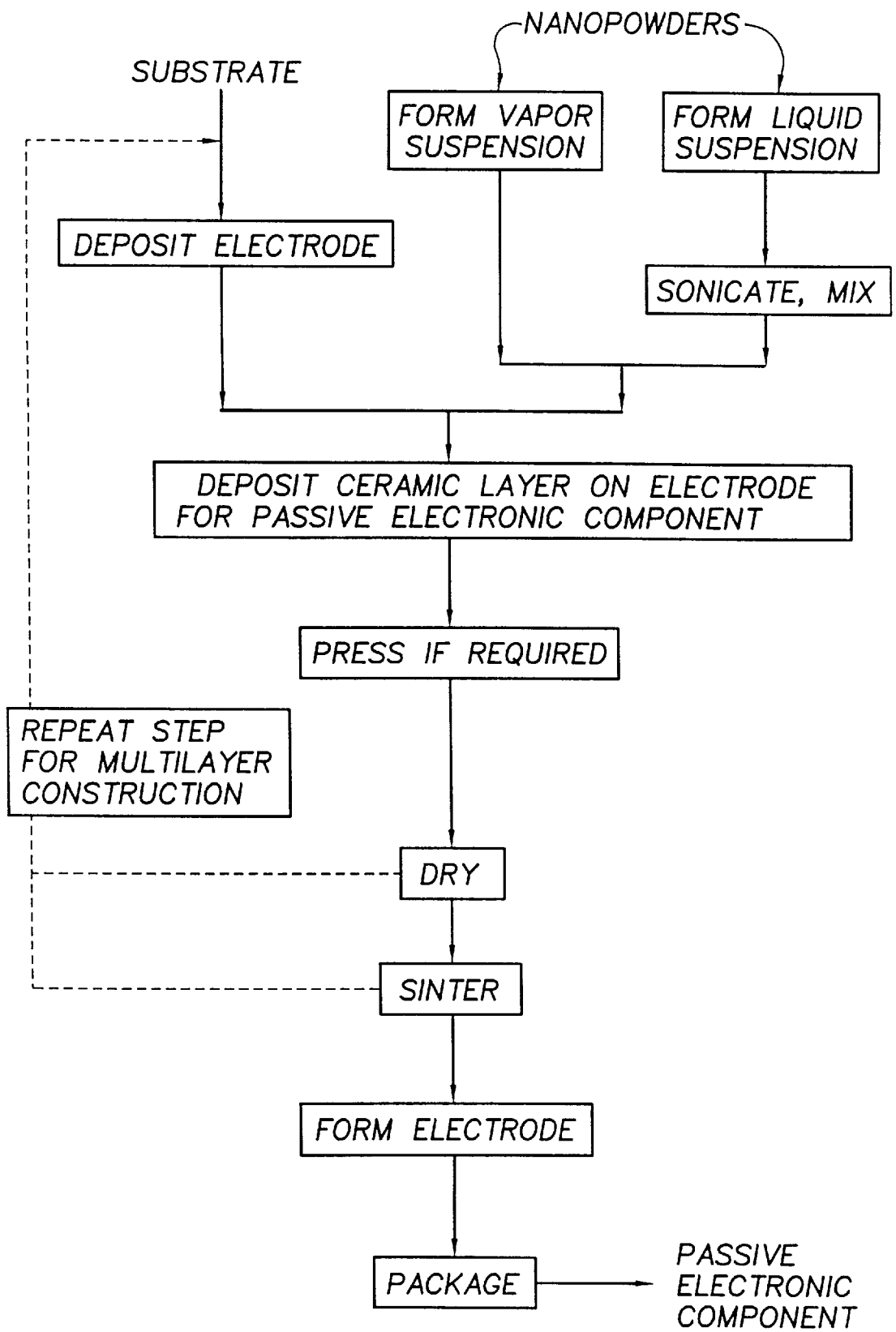
FIG. 23 is a flow diagram of the steps of the invention applicable to the manufacture of all electronic passive components.

Thus, this disclosure demonstrates that electrode/ceramic layers for passive electronic components with properties markedly superior to those exhibited from prior-art processes can be achieved when nanopowders are used and nanostructured layers are produced. In its broadest form, applicable to the manufacture of all electronic passive components, the invention can be described by the steps illustrated in FIG. 23. The critical steps consist of the deposition of at least one ceramic layer from a nanopowder under conditions that will produce a nanostructured film. For multilayer devices, additional alternate layers of electrode and ceramic are deposited either before of after sintering of each layer, as indicated by the dotted lines in the figure's flow chart. These steps are the ones that produce the exceptional passive-electronic-component properties rendered possible by the invention.

Inasmuch as one of the primary inventive concepts of the invention is the utilization of nanosize powders produced by ultra-rapid expansion of a vaporized suspension of the feed material, as described in the referenced copending applications, and the attendant process advantages in fabricating layered dielectric components, it is clear that the concept could be applied as well to the fabrication of other any passive electronic components. Thus, as those skilled in the art would readily understand, the layer deposition process of the invention can be used to form other electrical and electronic components from nanoscale materials. Illustrative devices include piezoelectrics, piezomagnetics, thermistors, thyristors, magnetoelectronic, electro-optic and magneto-optical devices. It is also understood that specific changes in materials and procedures may be made by one skilled in the art to produce equivalent results.

Similarly, it is noted that the methods of assembly or deposition of nanoparticles to form structures according to this invention may vary depending on the particular application. For example, dry particles may be pressed into a structure of predetermined geometry, or may be deposited over a supporting substrate according to any known vapor deposition processes. The process of deposition may also be incorporated with the process of manufacture of the nano-size particles disclosed in the referenced copending applications. This method may be preferred for some applications because it enables the continuous fabrication of product from micron-sized raw material. According to the teachings of those applications, a thermal reactor system is used to produce nanoscale powders by ultra-rapid thermal quench processing of high-temperature vapors through a boundary-layer converging-diverging nozzle. A gas suspension of micron-sized feed material is continuously fed to a thermal reaction chamber and vaporized under conditions that minimize superheating and favor nucleation of the resulting vapor. The high temperature vapor is quenched by passing the vapor stream through the nozzle immediately after the initial nucleation stages, thereby rapidly quenching it through expansion at rates of at least 1,000° C. per second, preferably greater than 1,000,000° C. per second, to block the continued growth of the nucleated particles and produce a nanosize powder suspension of narrow particle-size distribution. A gaseous boundary-layer stream is preferably also injected to form a blanket over the internal surface of the nozzle to prevent vapor condensation in the throat of the nozzle. A receiving substrate is placed in the diverging section of the nozzle to receive the nanoparticles produced in the quenched stream. Thus, a nanostructured layer of dielectric material can be deposited directly as desired on the particular device being manufactured. As one skilled in the art would readily understand, the precise location of the substrate within the nozzle, the residence time of the substrate, and other operating parameters can be manipulated to produce the physical structure desired for a particular application.

Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent apparatus and methods.

What we claim is:

1. A process for producing a ceramic-layer structure for passive electronic components comprising the following steps:

preparing a suspension of ceramic material in powder form having particle size smaller than the largest one of mean free path, domain size or skin depth in said ceramic material;

depositing said powder of ceramic material over a substrate to form a nanostructured ceramic layer;

sintering said ceramic layer at a temperature sufficient to densify the ceramic layer;

and processing the ceramic layer to from the passive electronic component.

2. The process of claim 1, wherein said ceramic material in powder form consists of particles having an average grain size less than about 100 nm with a standard deviation less than about 25 nm.

3. The process of claim 1, wherein said sintering temperature is less than about 1,050° C.

4. The process of claim 1, wherein said ceramic material in powder form consists of particles having an average grain size less than about 100 nm with a standard deviation less than about 25 nm, and said sintering temperature is less than about 1,050° C.

5. The process of claim 1, wherein said sintering temperature is less than 950° C.

6. The process of claim 1, wherein said ceramic material in powder form consists of particles have an average grain size less than about 100 nm with a standard deviation less than about 25 nm, and said sintering temperature is less than 950° C.

7. The process of claim 1, further comprising the step of pressing said nanostructured ceramic layer after the deposition step.

8. The process of claim 1, wherein said suspension of ceramic material consists of a liquid suspension; and further comprising the step of sonicating the suspension prior to the deposition step.

9. The process of claim 8, further comprising the step of pressing said nanostructured ceramic layer after the deposition step.

10. The process of claim 1, further comprising the steps of depositing a predetermined number of alternate electrode and ceramic layers over said nanostructured ceramic layer prior to performing the sintering step, so as to produce a multilayered structure.

11. The process of claim 1, further comprising the steps of depositing an electrode layer over said nanostructured ceramic layer after the sintering step, depositing a new ceramic layer over said electrode layer, sintering said new ceramic layer, and repeating these steps to form a multilayered structure.

12. A process for producing a ceramic-layer structure for passive electronic components from a precursor ceramic material, comprising the following steps:

evaporating the precursor ceramic material in a gaseous atmosphere in a thermal reactor, thereby creating a vapor/gas mixture;

quenching said vapor/gas mixture by effecting its expansion through a pressure drop, thereby causing the formation of a nanopowder of ceramic material in a product gas, the nanopowder having particle size smaller than the largest one of mean free path, domain size or skin depth in said ceramic material;

separating said nanopowder of ceramic material from said product gas;

depositing the nanopowder of ceramic material over a supporting substrate to form a ceramic layer;

sintering said ceramic layer at a temperature sufficient to densify said ceramic layer;

and processing the ceramic layer to from the passive electronic component.

13. The process of claim 12, wherein said nanopowder consists of particles having an average grain size less than about 100 nm.

14. The process of claim 12, wherein said sintering temperature is less than about 1,100° C.

15. The process of claim 12, wherein said nanopowder consists of particles having an average grain size less than about 100 nm and said sintering temperature is less than about 1,100° C.

16. The process of claim 12, wherein said sintering temperature is less than about 950° C.

17. The process of claim 12, wherein said nanopowder consists of particles having an average grain size less than about 100 nm and said sintering temperature is less than about 950° C.

18. A process for producing a dielectric-layer structure for capacitors comprising the following steps:

depositing a layer of electrode material over a supporting substrate to form a first electrode layer;

depositing nanoscale particles of dielectric material over said electrode layer to form a dielectric layer, the nanoscale particles having particle size smaller than the largest one of mean free path, domain size or skin depth in said dielectric material;

depositing another layer of electrode material over said dielectric layer to form a second electrode layer;

sintering said dielectric layer at a temperature sufficient to densify the dielectric layer; and processing then dielectric layer structure to form the capacitor.

19. The process of claim 18 wherein said nanoscale particles have an average grain size less than about 100 nm.

20. The process of claim 18, wherein said electrode material is silver and said temperature is less than about 950° C.

21. The process of claim 18, wherein said nanoscale particles have an average grain size less than 100 nm, said electrode material is silver and said temperature is less than 950° C.

* * * * *